United States Patent [19]
Klein et al.

[11] Patent Number: 5,562,620
[45] Date of Patent: Oct. 8, 1996

[54] PERFUSION SHUNT DEVICE HAVING NON-DISTENSIBLE POUCH FOR RECEIVING ANGIOPLASTY BALLOON

[75] Inventors: Enrique J. Klein, Los Altos; Philip C. Evard, Palo Alto, both of Calif.

[73] Assignee: Localmed, Inc., Palo Alto, Calif.

[21] Appl. No.: 401,541

[22] Filed: Mar. 10, 1995

Related U.S. Application Data

[63] Continuation-in-part of Ser. No. 305,250, Sep. 13, 1994, which is a continuation-in-part of Ser. No. 221,613, Apr. 1, 1994.

[51] Int. Cl.$^6$ ..................................................... A61M 29/00
[52] U.S. Cl. .......................... 604/96; 604/102; 604/264; 604/53
[58] Field of Search .................................. 604/96, 21, 53, 604/104, 97, 103, 52, 107, 49, 28, 266, 264, 101; 606/108, 192, 194; 623/1

[56] References Cited

U.S. PATENT DOCUMENTS

| | | |
|---|---|---|
| 3,173,418 | 3/1965 | Baran . |
| 3,394,705 | 7/1968 | Abramson . |

(List continued on next page.)

FOREIGN PATENT DOCUMENTS

| | | |
|---|---|---|
| WO92/11890 | 7/1992 | WIPO . |
| WO92/11895 | 7/1992 | WIPO . |
| WO93/21985 | 11/1993 | WIPO . |
| WO94/11048 | 5/1994 | WIPO . |
| WO94/11053 | 5/1994 | WIPO . |
| WO95/03081 | 2/1995 | WIPO . |
| WO95/03082 | 2/1995 | WIPO . |

OTHER PUBLICATIONS

Bom, N. et al. "Early and recent intraluminal ultrasound devices," 1989, Internal Journal of Cardiac Imaging 4:79–88.

Advanced Cardiovascular Systems, Inc., Temecula, California, "ACS Rx Perfusion™ Coronary Dilatation Catheter," 1990, (Product Brochure) pp. 1–23.

Hong, M. K. et al., "A New PTCA Balloon Catheter With Intramural Channels For Local Delivery of Drugs at Low Pressure," 1992, Supplement to Circulation, Abstracts From the 65th Scientific Sessions, Vol. 86, No. 4, #1514.

EndoSonics, Pleasanton, California, "The Cathscanner® Intracoronary Imaging System," 1992, (Product Brochure).

SCIMED®, Maple Grove, Minnesota, "Dispatch™," 1994, (Product Brochure).

Package inset "ACS RX Persuion™ Coronary Dilatation Catheter," Advanced Cardiovascular Systems, Inc. copyright 1990, pp. 1–23.

*Primary Examiner*—C. Fred Rosenbaum
*Assistant Examiner*—Perry E. Van Over
*Attorney, Agent, or Firm*—Townsend and Townsend and Crew LLP

[57] ABSTRACT

A perfusion shunt device is used in conjunction with balloon catheters to provide blood perfusion across an inflated balloon in a blood vessel. The perfusion shunt device comprises a flexible conduit structure having one or more blood perfusion paths formed from a proximal end to a distal end thereof. The flexible conduit structure is usually attached directly or indirectly to a proximal shaft structure. Discrete anchors or expansible sleeves or cages are provided for locating the conduit structure over the balloon on the catheter. The flexible conduit structure will not be directly attached to the balloon, but rather will be secured at locations distal to an proximal of the balloon. In this way, constriction and distortion of the conduit structure and/or balloon resulting from balloon expansion are minimized. The device may be loaded over a conventional angioplasty balloon catheter outside of the blood vessel being treated, either before or after an angioplasty procedure. In an alternative embodiment, a non-distensible pouch is formed integrally with the flexible conduit structure in order to receive the balloon of a balloon angioplasty catheter. The non-distensible nature of the pouch limits balloon inflation size to reduce the chance of injuring the blood vessel.

69 Claims, 19 Drawing Sheets

U.S. PATENT DOCUMENTS

| | | |
|---|---|---|
| 3,938,502 | 2/1976 | Bom . |
| 4,292,974 | 10/1981 | Fogarty et al. . |
| 4,323,071 | 4/1982 | Simpson et al. . |
| 4,327,721 | 5/1982 | Goldin et al. . |
| 4,406,656 | 9/1983 | Hattler et al. . |
| 4,417,576 | 11/1983 | Baran . |
| 4,437,856 | 3/1984 | Valli . |
| 4,576,177 | 3/1986 | Webster, Jr. . |
| 4,661,094 | 4/1987 | Simpson . |
| 4,681,564 | 7/1987 | Landreneau . |
| 4,693,243 | 9/1987 | Buras . |
| 4,744,790 | 5/1988 | Jankowski et al. . |
| 4,762,129 | 8/1988 | Bonzel . |
| 4,775,371 | 10/1988 | Mueller, Jr. . |
| 4,776,337 | 10/1988 | Palmaz . |
| 4,790,315 | 12/1988 | Mueller, Jr. et al. . |
| 4,841,977 | 6/1989 | Griffith et al. . |
| 4,850,358 | 7/1989 | Millar . |
| 4,850,969 | 7/1989 | Jackson . |
| 4,877,031 | 10/1989 | Conway et al. . |
| 4,892,519 | 1/1990 | Songer et al. . |
| 4,911,163 | 3/1990 | Fina . |
| 4,917,097 | 4/1990 | Proudian et al. . |
| 4,950,232 | 9/1990 | Ruzicka et al. . |
| 4,976,689 | 12/1990 | Buchbinder et al. . |
| 4,994,033 | 2/1991 | Shockey et al. . |
| 5,000,734 | 3/1991 | Boussignac et al. . |
| 5,007,897 | 4/1991 | Kalb et al. . |
| 5,009,636 | 4/1991 | Wortley et al. . |
| 5,015,232 | 5/1991 | Maglinte . |
| 5,019,042 | 5/1991 | Sahota . |
| 5,021,044 | 6/1991 | Sharkawy . |
| 5,034,001 | 7/1991 | Garrison et al. . |
| 5,041,089 | 8/1991 | Mueller et al. . |
| 5,046,497 | 9/1991 | Millar . |
| 5,049,132 | 9/1991 | Shaffer et al. . |
| 5,087,244 | 2/1992 | Wolinsky et al. . |
| 5,087,247 | 2/1992 | Horn et al. . |
| 5,092,877 | 3/1992 | Pinchuk . |
| 5,102,390 | 4/1992 | Crittenden et al. . |
| 5,102,415 | 4/1992 | Guenther et al. . |
| 5,112,305 | 5/1992 | Barath et al. . |
| 5,117,831 | 6/1992 | Jang et al. . |
| 5,163,921 | 11/1992 | Feiring . |
| 5,180,364 | 1/1993 | Ginsburg . |
| 5,180,366 | 1/1993 | Woods . |
| 5,180,368 | 1/1993 | Garrison . |
| 5,192,307 | 3/1993 | Wall . |
| 5,203,338 | 3/1993 | Jang . |
| 5,213,576 | 5/1993 | Abiuso et al. . |
| 5,219,326 | 6/1993 | Hattler . |
| 5,219,335 | 6/1993 | Willard et al. . |
| 5,226,888 | 7/1993 | Arney . |
| 5,242,396 | 9/1993 | Evard . |
| 5,254,089 | 10/1993 | Wang . |
| 5,257,974 | 11/1993 | Cox . |
| 5,266,073 | 11/1993 | Wall . |
| 5,281,200 | 1/1994 | Corso, Jr. et al. . |
| 5,282,785 | 2/1994 | Shapland et al. . |
| 5,284,473 | 2/1994 | Calabria . |
| 5,295,962 | 3/1994 | Crocker et al. . |
| 5,300,085 | 4/1994 | Yock . |
| 5,306,250 | 4/1994 | March et al. . |
| 5,308,356 | 5/1994 | Blackshear, Jr. et al. . |
| 5,318,535 | 6/1994 | Miraki . |
| 5,344,401 | 9/1994 | Radisch et al. . |
| 5,358,487 | 10/1994 | Miller . |
| 5,364,356 | 11/1994 | Höfling . |
| 5,370,617 | 12/1994 | Sahota . |
| 5,378,237 | 1/1995 | Boussignac et al. . |
| 5,395,333 | 3/1995 | Brill . |
| 5,415,637 | 5/1995 | Khosravi . |
| 5,425,709 | 6/1995 | Gambale . |
| 5,433,706 | 7/1995 | Abiuso . |
| 5,439,445 | 8/1995 | Kontos . |

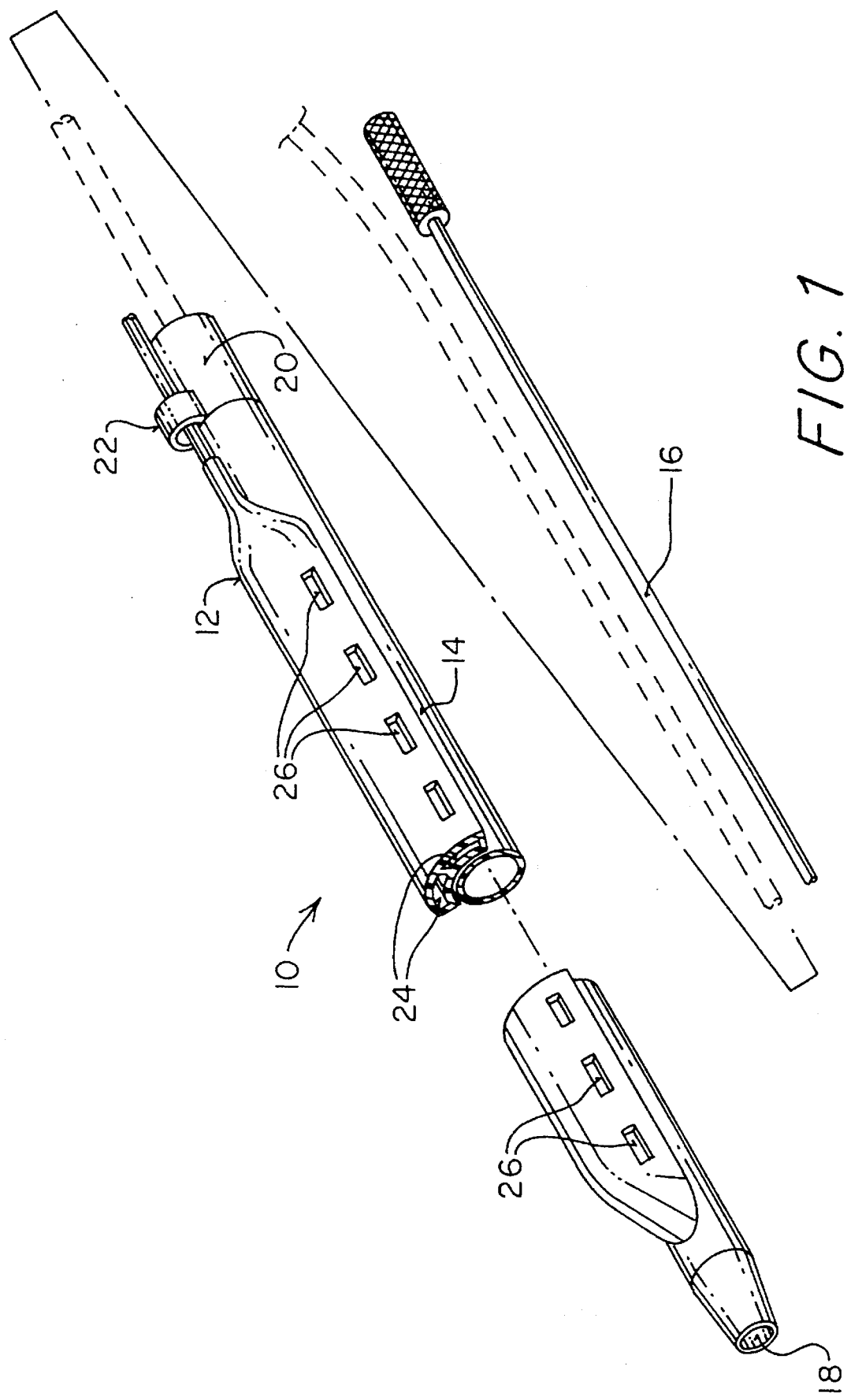

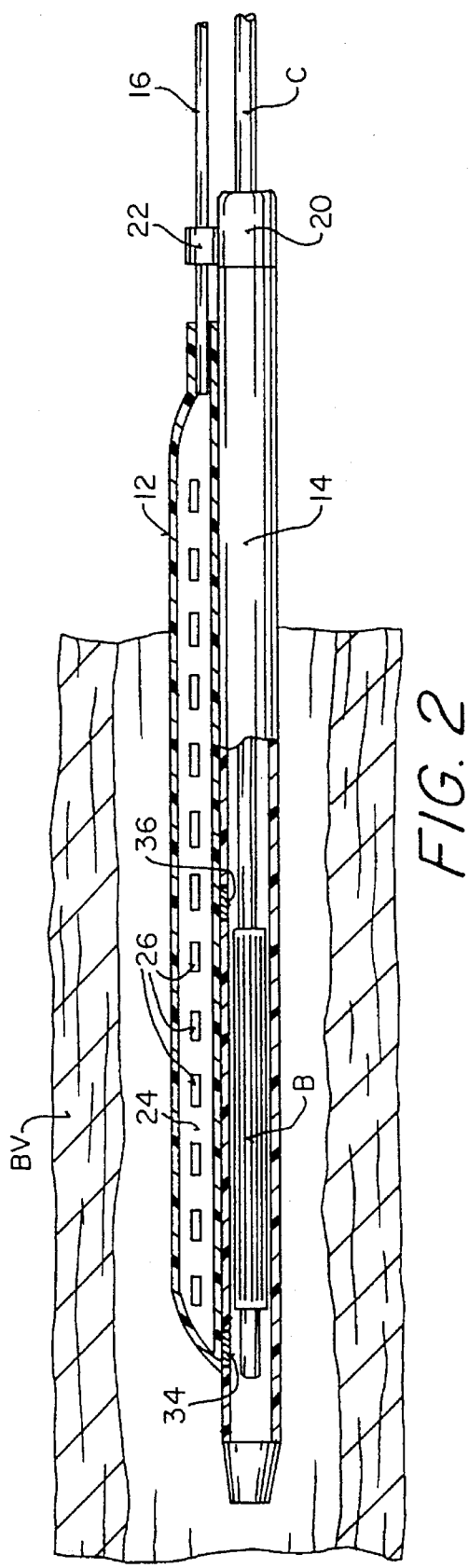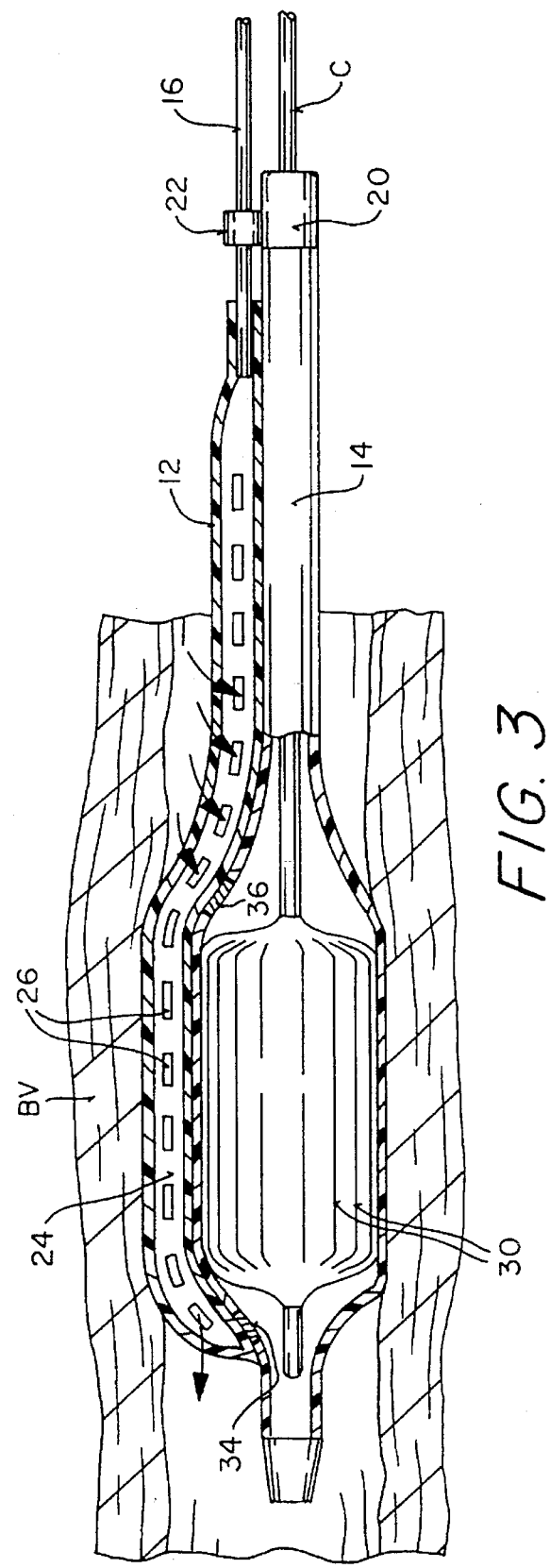

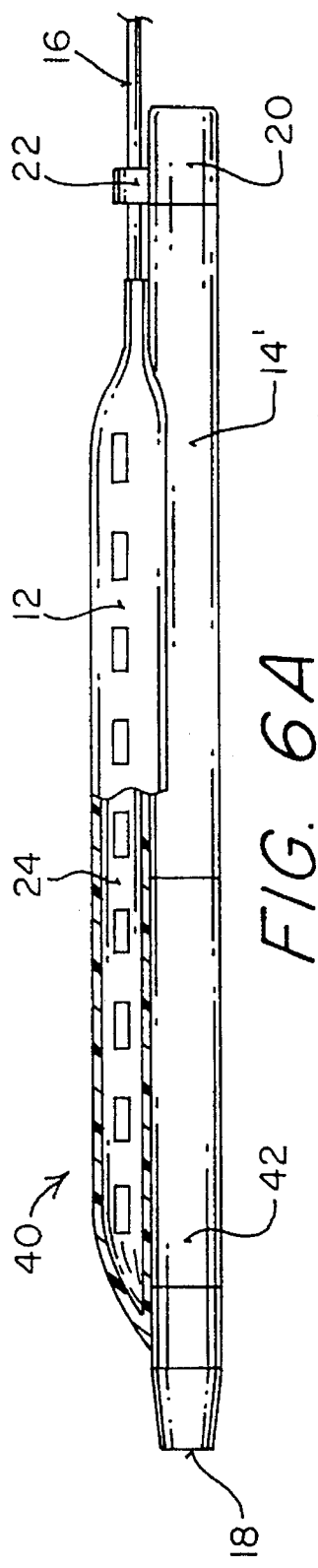
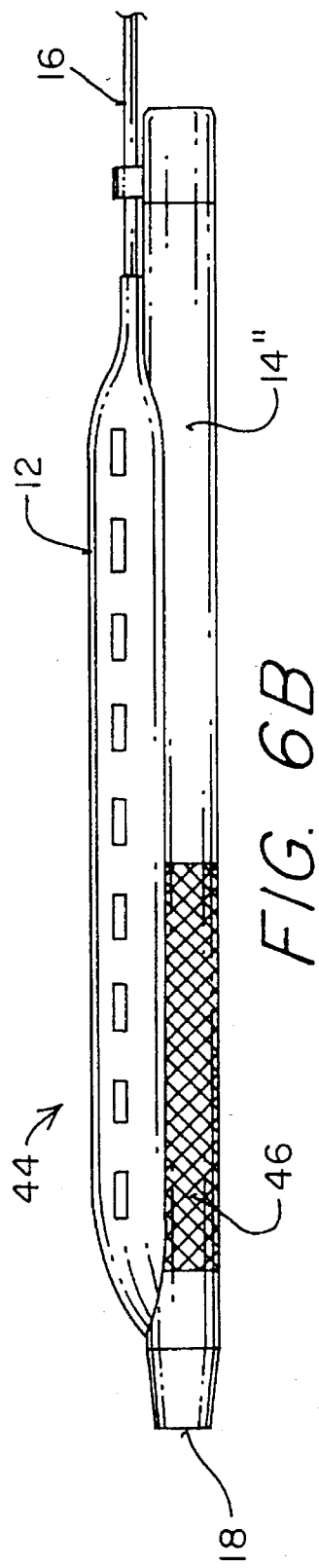
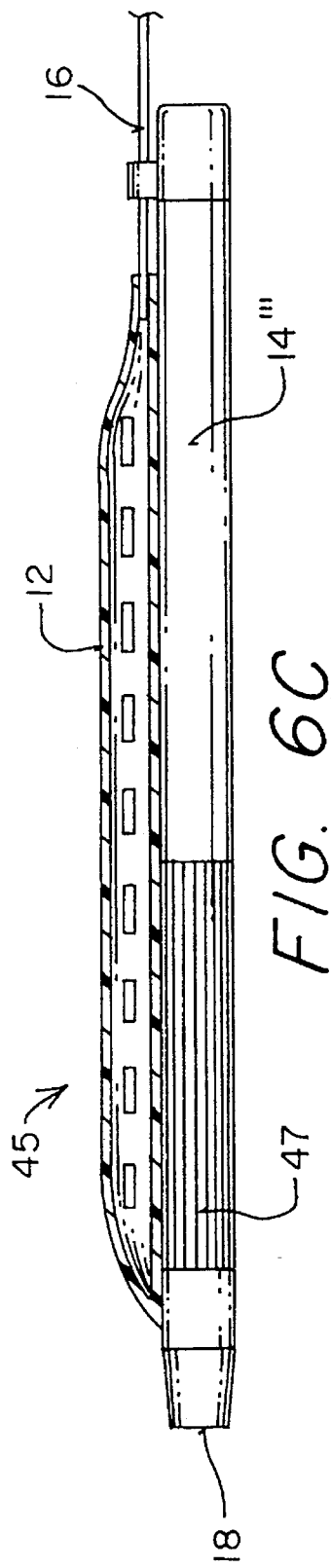

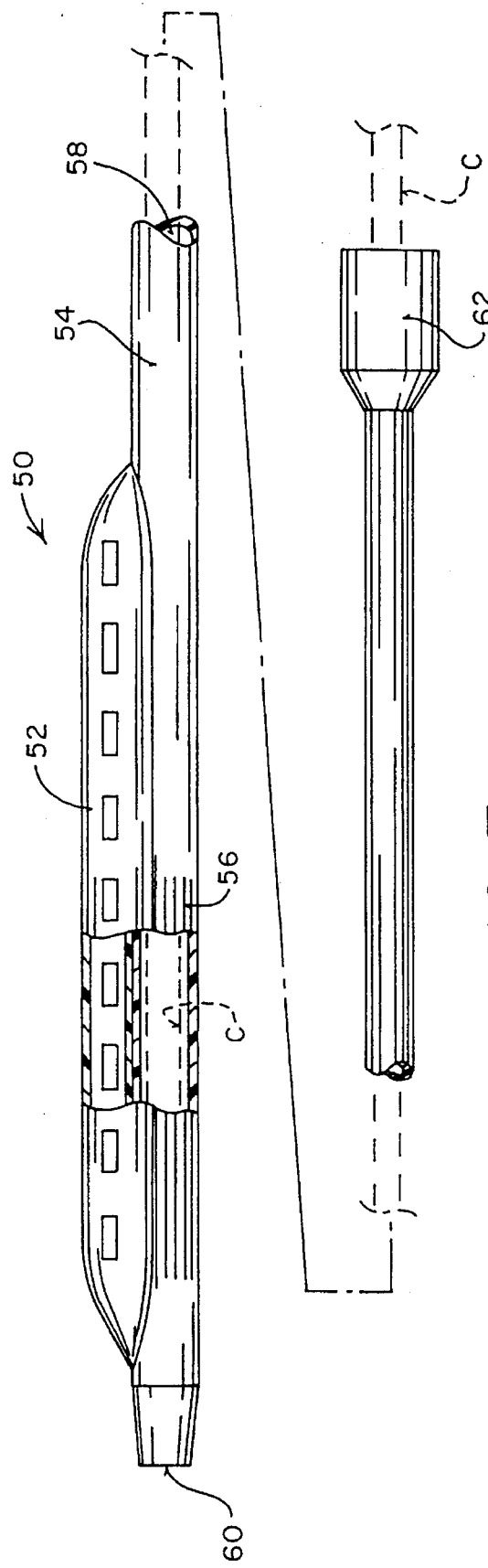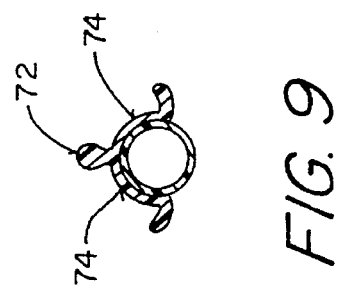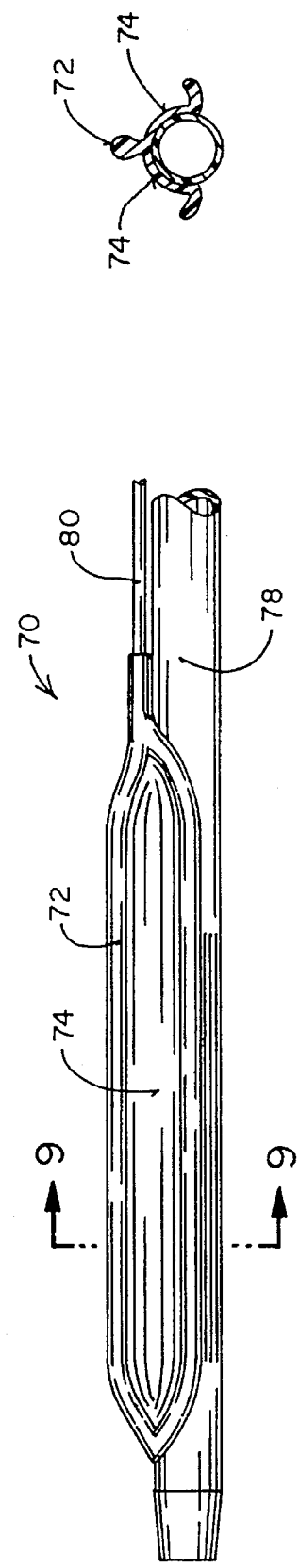
FIG. 7
FIG. 9
FIG. 8

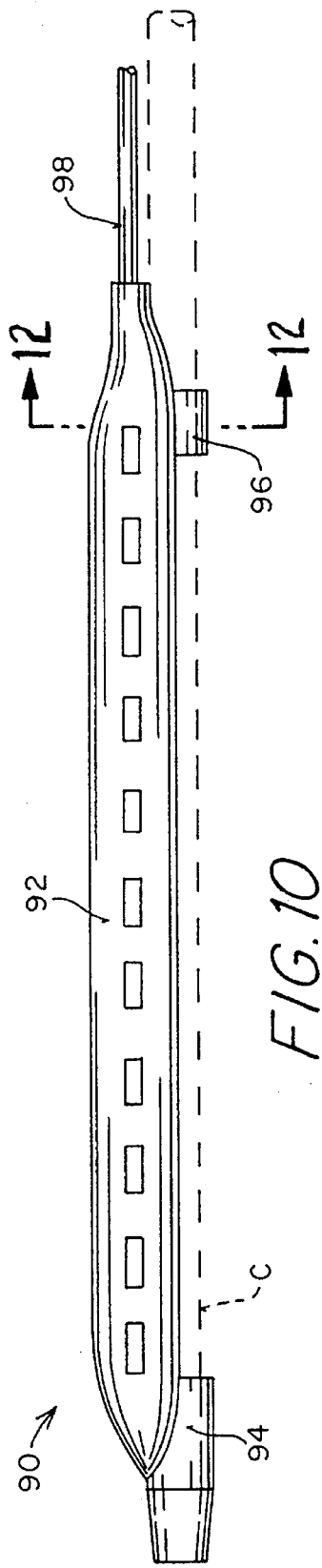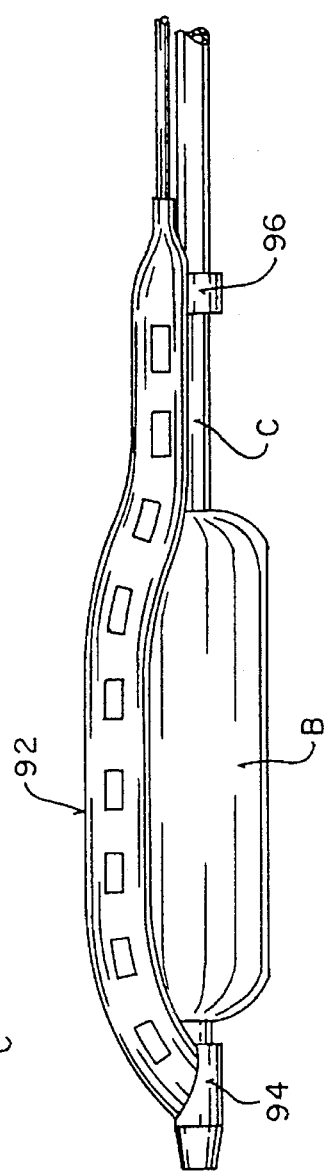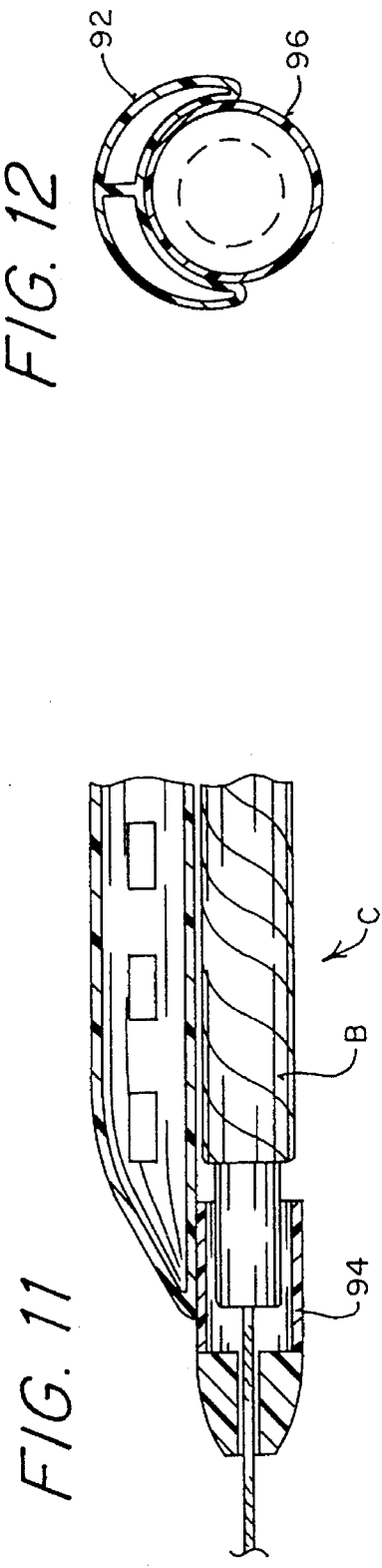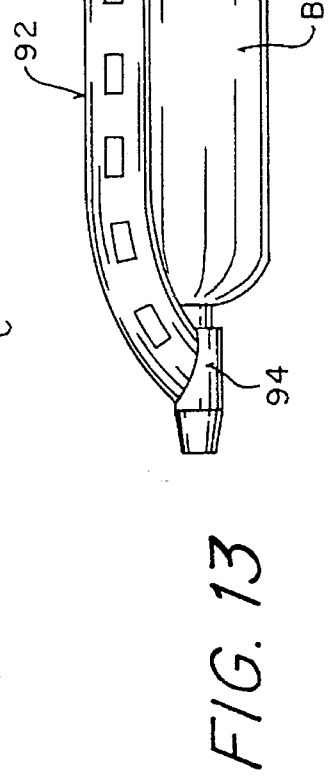

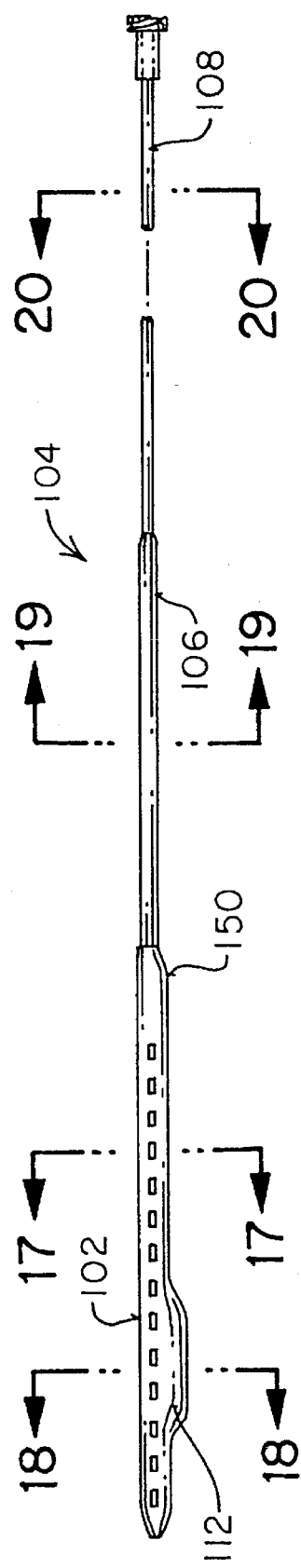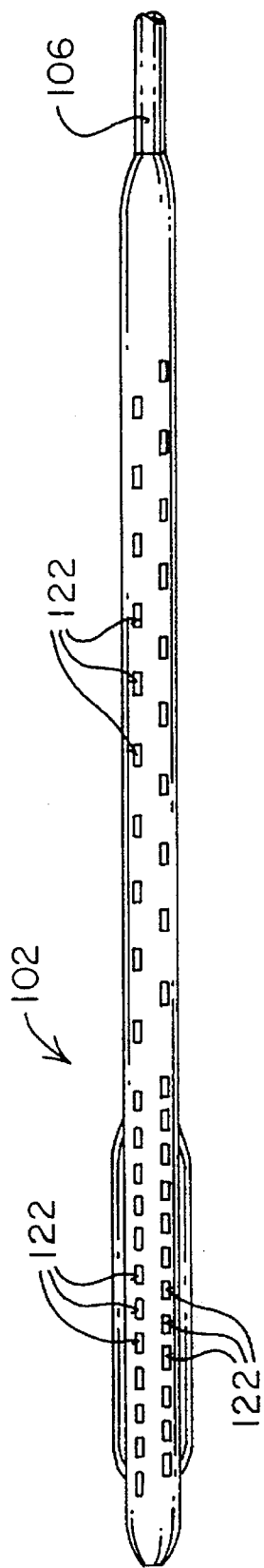
FIG. 15
FIG. 16

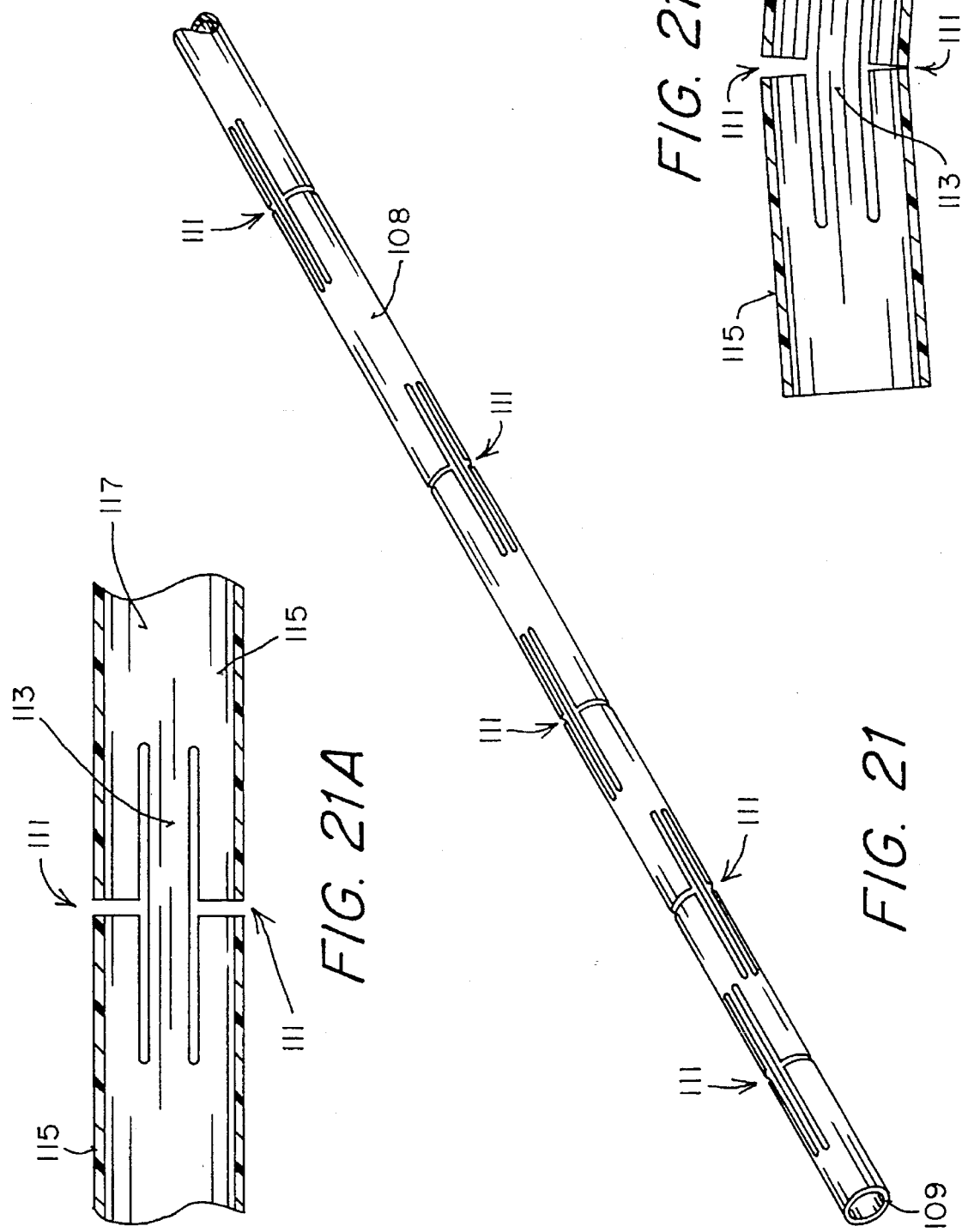

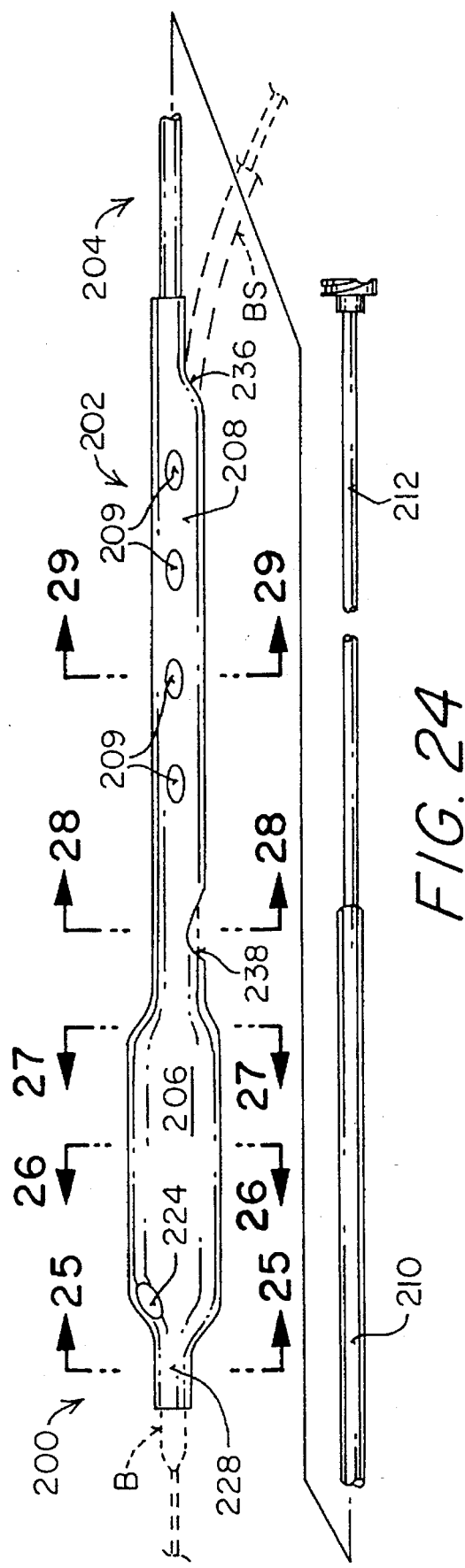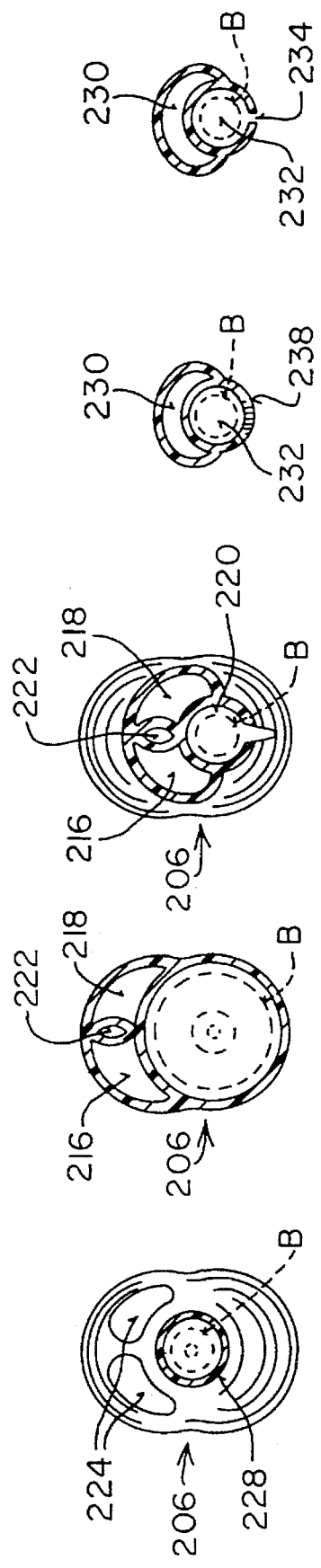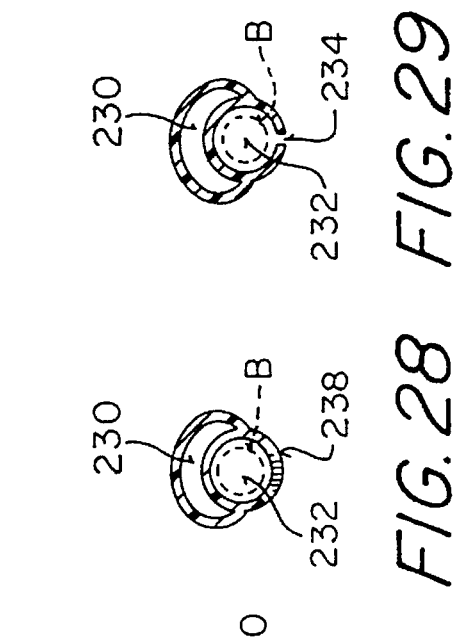

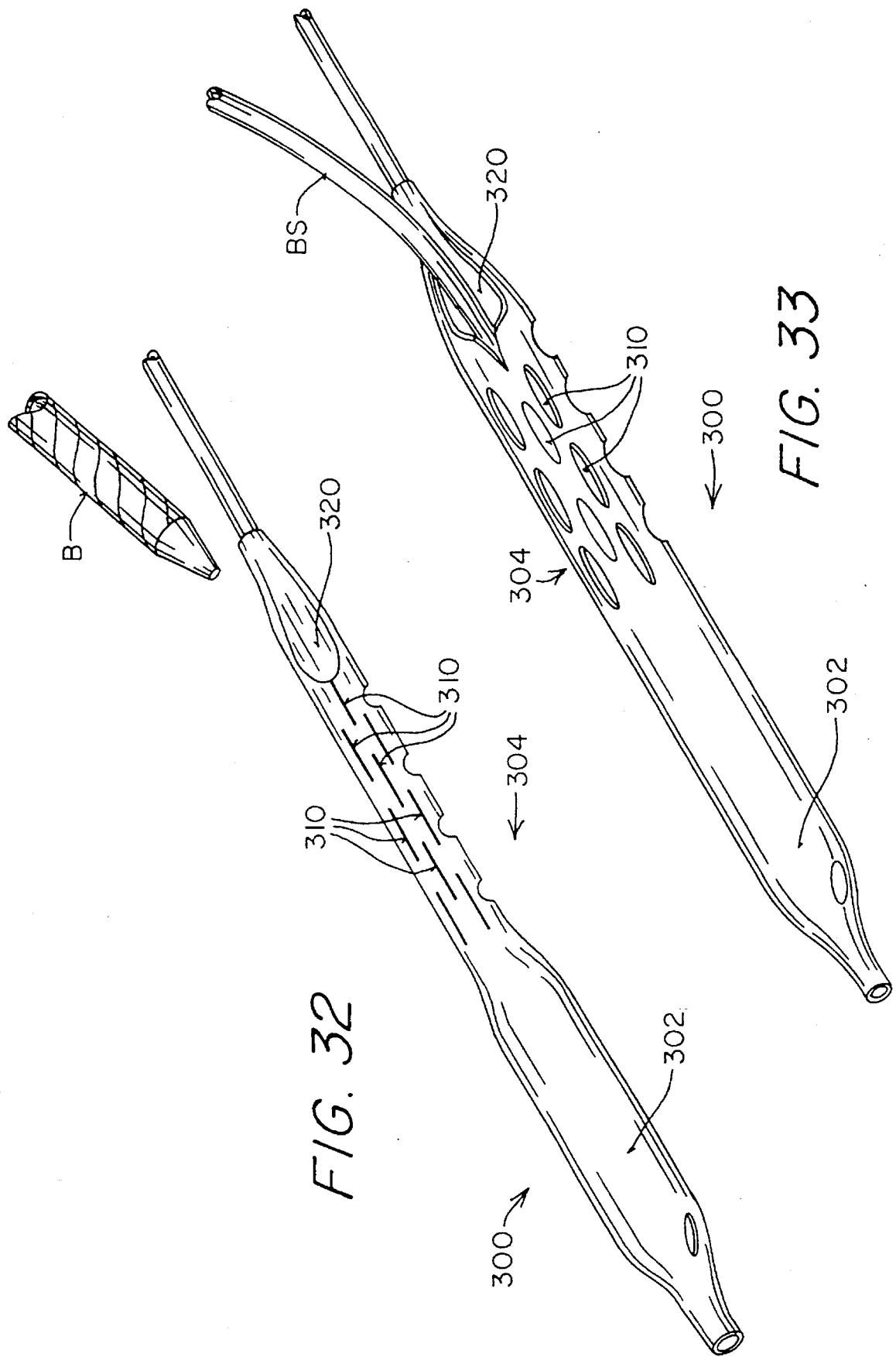

PERFUSION SHUNT DEVICE HAVING NON-DISTENSIBLE POUCH FOR RECEIVING ANGIOPLASTY BALLOON

CROSS-REFERENCE TO RELATED APPLICATION

This application is related to application Ser. No. 08/222,143, filed on Apr. 1, 1994, and is a continuation-in-part of application Ser. No. 08/305,250, filed on Sep. 13, 1994, which is a continuation-in-part of application Ser. No. 08/221,613, filed on Apr. 1, 1994, the full disclosures of which are incorporated herein by reference.

BACKGROUND OF THE INVENTION

1. Field of the Invention

This invention relates generally to intravascular dilatation devices, and more specifically to intravascular devices to provide blood flow during dilatation and other therapeutic and diagnostic procedures.

In percutaneous transluminal angioplasty procedures, a catheter having an expansible distal end, usually in the form of a balloon, is positioned in a lumen of a blood vessel with the distal end disposed within a stenotic atherosclerotic region of the vessel. The expansible end is then expanded to dilate the vessel and restore adequate blood flow through the diseased region. During dilation blood flow is interrupted, limiting inflation time to between 0.5 and 3 minutes.

While angioplasty has gained wide acceptance, it continues to be limited by two major problems, abrupt closure and restenosis. Abrupt closure refers to the acute occlusion of a vessel immediately after or within the initial hours following the dilation procedure. This complication, occurring in approximately one in twenty cases, frequently results in myocardial infarction and death if blood flow is not quickly restored. At present, arterial dissections, one of the causes of abrupt closure, are treated by prolonged balloon inflations lasting more than 5 minutes. Special angioplasty balloon catheters which allow for perfusion through the dilation catheter during inflation are required for this purpose.

Restenosis refers to the re-narrowing of an artery after an initially successful angioplasty. Restenosis usually occurs within the initial six months after angioplasty and afflicts approximately one in three cases. Therefore, approximately one-third of treated patients will require additional revascularization procedures. Many different strategies have been tried unsuccessfully to reduce the restenosis rate, including mechanical (e.g., prolonged balloon inflations, atherectomy, laser and stenting) and pharmacologic (e.g., calcium antagonists, ace inhibitors, fish oils, steroids and anti-metabolic) approaches. One promising new strategy is to delivery agent directly to the arterial wall at the site of angioplasty. Several devices have been developed to deliver agent locally into the arterial wall. Similar to angioplasty balloon catheters, balloon deployed drug delivery catheters interrupt blood flow, limiting the time available to deliver agent.

Thus, it would be desirable to provide perfusion and agent delivery capabilities to angioplasty catheters for the treatment of abrupt closure and restenosis and for other purposes.

2. Description of the Background Art

A sleeve catheter intended for drug delivery when placed over an angioplasty balloon is described in U.S. Pat. No. 5,364,356. A drug delivery catheter having an internal blood perfusion lumen and external drug delivery balloon is described in WO93/21985. U.S. Pat. Nos. 5,318,535; 5,308,356; 5,300,085; 5,284,473; 5,087,247; 4,892,519; and 4,790,315, describe angioplasty balloon catheters having integral blood perfusion capability. U.S. Pat. No. 4,661,094, describes a blood perfusion catheter intended primarily to provide blood flow through an occluded blood vessel. U.S. Pat. Nos. 5,163,921 and 5,180,364, describe guiding catheters having perfusion flow ports at their distal ends. Angioplasty catheters having integral blood perfusion capability are commercially available, e.g., under the tradename ACS Rx Perfusion™ Coronary Dilatation Catheter, from Advanced Cardiovascular Systems, Inc., Temecula, Calif., as described in a package insert copyright 1990. A balloon angioplasty catheter having a tapered mandrel removably received in an inflation lumen therein for enhancing column strength is disclosed in U.S. Pat. No. 5,242,396. A balloon catheter having perfusion conduits formed in the balloon itself is described in U.S. Pat. No. 5,000,734.

SUMMARY OF THE INVENTION

According to the present invention, apparatus and methods are provided for establishing perfusion blood flow past an expanded balloon in a blood vessel during angioplasty and related procedures. Optionally, the apparatus and methods may also provide for the delivery of therapeutic agents, contrast media, or any other desired liquid composition, to a vascular treatment site during angioplasty or at other times. Apparatus comprise a perfusion shunt device which includes a flexible conduit structure having one or more blood perfusion paths extending axially over at least a portion thereof. Usually, the flexible conduit structure comprises a perfusion tube having a proximal end, a distal end, and at least one blood perfusion lumen defining the blood perfusion path. The blood perfusion lumen includes a plurality of axially spaced-apart perfusion ports which permit blood flow into and out of the perfusion lumen.

The flexible conduit structure is adapted to be removably positioned and secured over the balloon of an angioplasty catheter. In a preferred embodiment, the flexible conduit structure includes a non-distensible pouch having an elongate balloon-receiving cavity. In a particularly preferred embodiment, the flexible conduit structure comprises a tubular body having both blood perfusion lumen(s) and a balloon-receiving lumen formed therein. The blood perfusion lumen(s) will extend from a proximal end to a distal end of the tubular body, while the balloon receiving lumen is disposed parallel to the perfusion lumen. The balloon-receiving lumen will preferably include an enlarged region in the form of a balloon-receiving pouch. The pouch will be deployable from a collapsed or folded configuration to an expanded configuration, but will be generally non-distensible in the radial direction after it is in its fully expanded configuration. The pouch will preferably be formed integrally with the remainder of the tubular body, having a flexible, slack wall which may be folded into the collapsed configuration and subsequently expanded by inflating a balloon therein.

In a first preferred aspect of the present invention, the perfusion shunt device further comprises a proximal shaft structure extending in the proximal direction from the flexible conduit structure. Preferably, the proximal shaft structure includes a more flexible distal portion (intended to be positioned in the guide catheter within the aortic arch and having a length from 10 cm to 25 cm and a diameter below 1.5 mm) and a less flexible proximal portion (intended to be disposed in the guide catheter within the femoral artery leading to the aortic arch and having a length from 80 cm to 120 cm and a diameter below 1 mm) when the device is used in coronary procedures with a femoral approach. In this context, shaft flexibility relates to its bending stiffness, where a more flexible portion of the shaft will have a lower bending stiffness, usually defined by the flexural modulus. Optionally, a transition may be provided between the more flexible distal portion and less flexible proximal portion, where the stiffness increases over the preselected length, usually being at least 1 cm in length, typically being in the range from 2 cm to 10 cm, in the proximal direction. The transition region provides a strain relief and reduces the tendency of the shaft to kink or collapse at an abrupt transition between the adjacent portions having differing stiffnesses. In coronary procedures, the flexible conduit structure will have a length sufficient to extend from a coronary ostium to a distal location within the coronary vasculature.

In a further preferred aspect of the present invention, the proximal shaft structure will have a continuous lumen formed from its proximal end to its distal end. The lumen in the proximal shaft structure will be fluidly connected to the perfusion path(s) or lumen(s) within the flexible conduit structure in order to deliver a therapeutic agent, contrast media, perfusion fluid, flushing fluid, or any other desired liquid composition.

In yet a further preferred aspect of the present invention, the non-distensible pouch will have a size which is somewhat smaller than the fully inflated angioplasty balloon with which it is to be used. Preferably, the outer envelope size of the perfusion shunt device in the region of the balloon-receiving cavity will be generally the same as that of the angioplasty balloon when fully inflated and unconstrained. The ability to constrain the balloon and limit the deployed size of the perfusion shunt device is advantageous in several respects. In particular, the perfusion shunt device may be used with the same angioplasty balloon as was initially used in the patient, thus saving the expense of using a new balloon catheter. Subsequent inflation of the balloon within the perfusion shunt device, however, will be constrained (size-limited) by the shunt device, preventing further distention and possible damage to the blood vessel which might result if the blood vessel were exposed to a perfusion shunt device having a larger cross-sectional area, as would be needed to accommodate full inflation of the angioplasty balloon used for primary treatment within the non-distensible pouch.

As further variation of the present invention, it will be possible to provide a family, or set, of perfusion shunt devices intended for use with a single size of angioplasty balloons, where successive ones of the devices can provide incremental increases of envelope size. Thus, the treating physician will be able to select one, two, or more different expansion envelope sizes for the perfusion shunt device, while using a single angioplasty balloon catheter. With such constructions, the balloon lumen and pouch can be made strong enough so that they will not yield to balloon overpressure. Such a family of perfusion shunt devices may be fabricated to have expansion envelope sizes which increase by a fixed incremental amount, typically about 0.1 to 0.5 mm, usually about 0.25 mm.

While the deployable pouch of the perfusion shunt device may be used to constrain a balloon to prevent the resulting combination of perfusion shunt device and inflated balloon from exceeding the nominal perimeter of the inflated balloon by itself, or to increase the perimeter of the combination by a predetermined amount as described above, it will be further possible to enlarge even non-distensible pouches by applying sufficient pressure to exceed the yielding stress of the pouch material. It will be appreciated that materials normally considered to be non-distensible, such as polyethylene (PE), polyether block amide (PEBA), polyethyleneterphthalate (PET), and the like, have a yielding stress which permits distension when sufficient force is applied, e.g. when a pouch composed of the material is stressed beyond a threshold value characteristic of the material. Thus, the perfusion shunt devices of the present invention may be used with the balloon at a first expansion pressure which causes the perfusion shunt device to expand to an external envelope size which corresponds generally to the fully expanded perimeter of the angioplasty balloon, in order to avoid injury and over stretching of the blood vessel. In some cases, however, it may be desirable to further stretch the treatment site within the blood vessel (i.e., stretch beyond the expansion provided by the initial angioplasty procedure), particularly if the initial balloon dilatation caused a dissection in the blood vessel wall that could be treated by application of additional force to "tack up" the dissected portion of the vessel. The perfusion shunt device of the present invention will allow such further expansion by increasing the internal pressurization within the angioplasty balloon sufficiently so that the yielding stress of the "non-distensible" pouch material is exceeded. The angioplasty balloon may then be inflated further to provide an envelope size of the perfusion shunt device which is greater than that of the balloon. Alternatively, a perfusion shunt device having a larger envelope size can be selected from a group of devices having different envelope sizes to provide incrementally greater dilatation, thus avoiding the need to stress yield the pouch.

According to the method of the present invention, the angioplasty balloon will be inflated within the non-distensible pouch of the flexible conduit structure at a treatment site within the patient's blood vessel. The blood flow paths (channels and/or lumens) in or over the flexible conduit structure will permit blood perfusion to the distal myocardium in cardiac procedures as well as optionally providing for infusion of therapeutic agents, contrast media, and other fluids. The method particularly provides for deployment of the non-distensible pouch by balloon inflation to a first pressure where the expanded envelope size of the flexible conduit structure is approximately equal to that of the fully inflated, unconstrained angioplasty balloon. Optionally, the angioplasty balloon may be inflated to a second pressure which exceeds the yielding stress of the pouch material so that the envelope size of the flexible conduit can be incrementally increased. Alternatively, a perfusion shunt device having a larger envelope size can be exchanged for the first device to provide such an increase in size. The flexible conduit structure may be introduced together with the angioplasty catheter (usually disposed proximally of the balloon) as the angioplasty balloon is introduced to the treatment site. Alternatively, the angioplasty catheter may be withdrawn from the patient following an angioplasty procedure, and the perfusion shunt device positioned over the angioplasty balloon outside the patient. The perfusion shunt device and catheter may then be reintroduced to the patient, typically over a guidewire in a generally conventional manner.

BRIEF DESCRIPTION OF THE DRAWINGS

FIG. 1 is a perspective view of a perfusion shunt device constructed in accordance with the principles of the present invention and including a split-tube balloon-attachment structure and a rod-like proximal shaft structure connected directly to a flexible conduit structure.

FIG. 2 is an elevational view of a distal portion of the perfusion shunt device of FIG. 1 shown in a blood vessel over a non-expanded balloon.

FIG. 3 is a view similar to FIG. 2, except that the balloon is expanded to engage the flexible conduit structure against the interior wall of the blood vessel.

FIG. 6A is an elevational view of the distal end of an alternative embodiment of a catheter constructed in accordance with the principles of the present invention, wherein the balloon attachment structure includes an elastomeric tube.

FIG. 6B is an elevational view of the distal end of a third embodiment of a catheter constructed in accordance with the principles of the present invention, wherein the balloon attachment structure comprises an expansible mesh tube.

FIG. 6C is an elevational view of the distal end of a fourth embodiment of a catheter constructed in accordance with the principles of the present invention, wherein the balloon attachment structure comprises an expansible pouch formed from a non-compliant material.

FIG. 7 is an elevational view of a fourth embodiment of a catheter constructed in accordance with the principles of the present invention, wherein the balloon attachment structure comprises a sleeve tube which is axially slit near its distal end and which extends proximally to define the proximal shaft structure of the device.

FIG. 8 is an elevational view of the distal end of a fifth embodiment of a perfusion shunt device constructed in accordance with the principles of the present invention, wherein the flexible conduit structure includes axial blood perfusion channels over its surface.

FIG. 9 is a cross-sectional view taken along line 9—9 of FIG. 8.

FIG. 10 is an elevational view of the distal end of a sixth embodiment of a perfusion shunt device constructed in accordance with the principles of the present invention, wherein the balloon attachment structure consists of proximal and distal anchors which are secured over a balloon catheter.

FIG. 11 is a detailed view of the distal tip of the device of FIG. 10, shown in section with an uninflated balloon catheter in place.

FIG. 12 is a cross-sectional view taken along line 12—12 of FIG. 10.

FIG. 13 illustrates the device of FIG. 10 when in place over an inflated balloon.

FIG. 15 is a side, elevational view of the perfusion shunt device of FIG. 14.

FIG. 16 is a top view of a distal portion of the perfusion shunt device of FIGS. 14 and 15.

FIG. 21 is a detailed view of a slotted tubular member that can be used to provide controlled flexibility in a more rigid proximal section of the proximal shaft structure.

FIG. 21A is a cross-sectional view of a beam connection structure which provides the controlled flexibility in the tubular element of FIG. 21.

FIG. 21B is a cross-sectional view similar to FIG. 21A, where the beam connection structure is shown in a flexed configuration.

FIG. 24 is a side, elevational view of still another alternative embodiment of a perfusion shunt device constructed in accordance with the principles of the present invention.

FIG. 25 is a cross-sectional view taken along line 25—25 of FIG. 24.

FIG. 26 is a cross-sectional view taken along line 26—26 of FIG. 24.

FIG. 27 is a cross-sectional view taken along line 27—27 of FIG. 24.

FIG. 28 is a cross-sectional view taken along line 28—28 of FIG. 24.

FIG. 29 is a cross-sectional view taken along line 29—29 of FIG. 24.

FIG. 32 and 33 illustrate the introduction of a balloon angioplasty catheter into a perfusion shunt device having an alternative reduced profile balloon-catheter-receiving lumen.

DESCRIPTION OF THE PREFERRED EMBODIMENT

Figure 5:
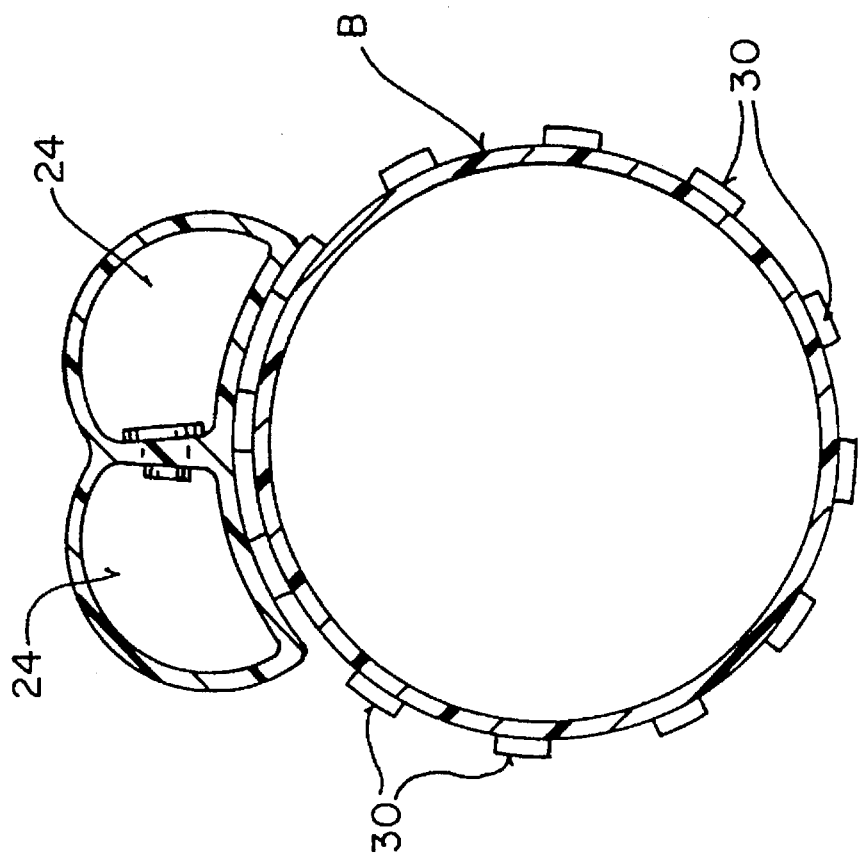
FIG. 5 is a view similar to FIG. 4, shown with an expanded balloon therein.

Perfusion shunt devices according to the present invention comprise a flexible conduit structure which may be positioned over an expansible balloon, typically a dilatation balloon on a vascular angioplasty catheter. The flexible conduit structure provides at least one, and often two or more, axial perfusion paths which permit blood flow over or through the flexible conduit structure when a balloon is expanded adjacent thereto. In the absence of the flexible conduit structure, the balloon would occlude the blood vessel lumen, thus preventing blood flow.

The flexible catheter structure will have a length sufficient to extend over the entire length of the catheter balloon when expanded. Preferably, the flexible conduit structure will have a length which is greater than that of the balloon so that a proximal portion of the flexible conduit structure will lie proximal of the expanded balloon over the vascular catheter to enhance blood perfusion inlet into the flow path(s). The length of the flexible conduit structure will be sufficient to accommodate the axial perfusion paths, being at least at least 2.5 cm, typically being in the range from 2.5 cm to 50 cm, preferably being from 10 cm to 40 cm, typically being from 10 cm to 30 cm. The diameter of the flexible conduit structure will be sufficiently small to pass from the coronary ostium into the coronary vasculature, typically being below 2 mm.

The axial perfusion path(s) will typically extend over a length of the flexible conduit structure which can be substantially greater than that of the balloon. Most conventional angioplasty balloons are only about 1.5 cm to 5 cm in length. The perfusion flow path(s) will usually be longer, typically being at least 10 cm, usually being from 10 cm to 30 cm. Most or all of the additional length (in excess of the balloon length) will usually (although not necessarily) be on the proximal side of the balloon so that there is ample region for blood to enter the flow paths upstream of the balloon when expanded.

The axial perfusion path(s) within the flexible conduit structure may be in the form of lumens, channels, or combinations thereof, and may be aligned axially, helically, or in any other pattern that will permit blood flow from the proximal side of the balloon to the distal side. As used herein, "lumen" generally refers to an enclosed flow path within the elongate conduit structure having a plurality of axially spaced-apart ports which permit the inflow and outflow of blood. "Channel" generally refers to an open structure having at least one axially continuous aperture which permits inflow and outflow of blood at all points. In all cases, the axial perfusion paths will permit inflow of blood at locations proximal (upstream) of the expanded balloon within the blood vessel and outflow of blood at locations distal (downstream) of the expanded balloon. Additionally, the axial flow paths may provide flow from and into branch blood vessels which would otherwise be blocked by expansion of the balloon. The flow paths will preferably provide a total cross-sectional flow area of at least 0.5 mm$^2$, preferably at least 0.6 mm$^2$, and usually in the range from 0.5 mm$^2$ to 1.2 mm$^2$, more usually from 0.6 mm$^2$ to 1 mm$^2$.

The number of axial perfusion paths will depend on a number of factors. Generally, for a given total luminal cross-sectional area, fewer paths will have a lesser total resistance to flow, thus enhancing the perfusion flow rate. Alternatively, fewer paths require a smaller total luminal cross-sectional area to carry a comparable flow with an identical pressure drop. While one perfusion path would be optimum if flow area and flow resistance were the only concerns, it is also necessary to conform the path(s) to the shape of the balloon and to provide internal reinforcement web(s) in order to inhibit collapse of the paths when the flexible conduit is pressed against the artery wall by the balloon. A particular two lumen design which provides an adequate flow area and low flow resistance while at the same time providing internal reinforcement is illustrated hereinafter.

The flexible conduit structure may be composed of a wide variety of biologically compatible materials, typically being formed from natural of synthetic polymers, such as polyvinylchloride, polyurethanes, polyesters, polyethylenes, polytetrafluoroethylenes (PTFE's), and nylons. A preferred material for the flexible conduit structures having an integral, non-distensible balloon-receiving pouch (see FIGS. 14–21 and the accompanying description) is polyether block amide (PEBA).

The flexible conduit structure will usually be non-compliant, and may optionally be reinforced to maintain patency of the flow paths during use. It will be appreciated that expansion of an adjacent balloon within the blood vessel will tend to collapse lumens, channels, and other flow paths within the flexible conduit structure. To maintain patency, reinforcement layers may be incorporated within the body in order to enhance strength, toughness, and the like. Exemplary reinforcement layers include metal fiber braid, polymeric fiber braid and the like. Optionally, the flexible conduit structure may be reinforced by closed inflation lumens, as described in parent application Ser. No. 08/221, 613, the full disclosure of which has previously been incorporated herein by reference, which are statically inflated to selectively strengthen the perfusion flow paths.

The flexible conduit structure will normally be formed by conventional extrusion of the desired polymeric material, forming one or more lumens, channels, or other perfusion path(s), as described in more detail hereinbelow. The cross-sectional areas and geometries of the perfusion path(s) within the conduit structure can be modified, if desired, by heat expansion and shrinkage using conventional techniques. Specific techniques for forming the conduit structures of the present invention are well-described in the patent and medical literature.

In a first set of embodiments as illustrated in FIGS. 1–13, the flexible conduit structure will be removably attached to the expansible balloon of a conventional vascular balloon catheter in such a way that the axial perfusion path(s) will extend over the balloon when the balloon is expanded within the lumen of a blood vessel. Conventional angioplasty balloon catheters are available from a number of commercial suppliers, such as Advanced Cardiovascular Systems, SciMed, C. R. Bard, Cordis, and others. Attachment of the flexible conduit structure to the balloon catheters will be such that the conduit structure is secured to the catheter only at locations proximal of and distal to the balloon. The flexible conduit structure will thus be free to shift position relative to the balloon as the balloon is radially expanded. Such freedom of motion provides a number of advantages. In particular, the freedom of relative movement lessens constriction and distortion of the conduit structure and the balloon. Additionally, the lack of direct attachment to the balloon combined with direct attachment to the catheter proximal to and distal of the balloon assures that the conduit structure will have a smooth, arcuate shape at both the proximal inlet and distal outlet of the flow paths. In some cases, the flexible conduit structure will be axially slidably attached to the underlying balloon catheter, particularly at location(s) proximal to the balloon (when the distal attachment points are axially fixed). Such an arrangement advantageously prevents the flexible conduit from disengaging at the distal attachment point (i.e., it cannot slide out of engagement), while permitting some axial movement at the proximal attachment locations(s) which enhances the ability of the conduit structure to conform to the underlying balloon in a smooth arc or curve.

Exemplary attachment structures include discrete anchors which are spaced-apart on opposite sides of the balloon, as well as expansible cage structures which are disposed directly over the balloon (but which are connected to the flexible conduit structure only at locations proximal of and distal to the region which receives the balloon). Such attachment structures are described in detail hereinbelow in connection with the figures.

In a second set of embodiments, as illustrated in FIGS. 14–20 and 22–34, the flexible conduit structure will be secured over the angioplasty balloon by a structural element which is attached to the conduit over the length of their common interface. Typically, the attachment structure will be a flexible, non-distensible pouch which is formed integrally with the flexible catheter structure, more typically being an expanded lumen thereof e.g., in a balloon-receiving lumen, where the balloon-receiving lumen usually has a length of at least 2.5 mm and the pouch will have a length in the range from 1.5 mm to 50 mm. The pouch will be highly flexible, permitting radial deployment when the associated angioplasty balloon is inflated therein. After the pouch has been expanded to its nominal envelope size during use, however, the material of the pouch or other containment structure will be non-distensible (absent sufficient pressurization of the angioplasty balloon to overcome the yielding stress of the material of an undersized balloon pouch). Thus, the nominal size of the pouch or other balloon-attaching structure will determine the final envelope size of the perfusion shunt device when a balloon is expanded therein (assuming that the balloon is at least large enough to deploy the pouch and that the balloon pressurization does not exceed the yielding stress of the pouch material). Thus, the perfusion shunt device can be used with an angioplasty balloon which, while by itself is optimally sized for the treatment site, might over distend the blood vessel if allowed to become fully inflated within the flexible conduit structure. By properly sizing the non-distensible pouch to constrain the balloon, such over distension of the blood vessel can be avoided.

In some cases, of course, it will be desirable to utilize the flexible conduit structure of the present invention to provide an expanded envelope size which is greater than the nominal size of the angioplasty balloon used in the primary procedure. This result can be achieved in particularly convenient ways. First, the material of the balloon pouch of the flexible conduit structure can be selected to have a yielding stress which will be exceeded when the internal inflation pressure of the internal angioplasty balloon exceeds a minimum threshold value within an undersized balloon pouch. Thus, the flexible conduit structure will have a first nominal envelope size which is achieved by balloon pressurization within a certain range, typically 2 atmospheres to 6 atmospheres. When the balloon is inflated above a threshold value at the upper end of this range, however, the yielding stress of the balloon pouch material will be exceeded, allowing the pouch to expand beyond its initial size. Such incremental expansion of the balloon pouch, of course, can be achieved in other ways as well. For example, it might be possible to form folds or pleats within the material of the pouch, where such folds or pleats are tacked together with sufficient strength so that they will maintain a first envelope size for all balloon inflation pressures up to a balloon inflation threshold value. When the threshold value is exceeded, the means securing the fold or pleats (e.g. an adhesive) will fail, allowing the pouch to further expand to a second, nominal expansion size.

A second preferred approach for enlarging the effective envelope size of the flexible conduit structure would be to employ two or more such structures, where the structures differ in the size increment provided by the conduit structure when inflated by an angioplasty balloon. Such differences in incremental size are preferably achieved by employing different pouch sizes in the flexible conduit structure, where each pouch size is undersized by a different incremental amount relative to the fully expanded balloon size. Thus, the same angioplasty balloon can be used to provide different effective diameters by selectively employing different flexible conduit structures constructed in accordance with the principles of the present invention. Frequently, for a given nominal angioplasty balloon size, a plurality of different flexible conduit structures may be provided to give the physician the opportunity of employing a range of envelope sizes, typically with nominal diameters sized incrementally by from 0.1 mm to 0.5 mm, usually by about 0.25 mm. The availability of flexible conduit structures having different effective envelope sizes is particularly useful when it is necessary to treat blood vessel dissections using a slightly larger equivalent balloon size.

A proximal shaft structure will usually be connected directly or indirectly to the flexible conduit structure (although in some designs it will be possible to secure the flexible conduit over a balloon without providing any proximal structure attached to the conduit). The shaft structure is preferred to permit manipulation of the flexible conduit structure by the treating physician. Thus, the proximal shaft structure will be sufficiently long to extend from the conduit structure over the entire length of the balloon catheter and outward through the guide catheter so that it can be accessible. In a first embodiment, the shaft structure is a small-diameter rod or hypotube, typically having a diameter below 1 mm, preferably below 0.8 mm usually between 0.8 mm and 0.7 mm for hypotube and between 0.6 mm and 0.4 mm for a rod structure. The rod may be attached directly to the flexible conduit structure and will be disposed parallel to the proximal body of the balloon catheter which extends outward through the vasculature. In the embodiment illustrated hereinafter, the proximal shaft will be secured to the proximal end of the flexible conduit. In many cases (not illustrated) it may be preferred to extend the shaft structure axially through the entire flexible conduit structure, typically through a dedicated lumen, in order to enhance the attachment.

Alternatively, the proximal shaft structure may comprise a tubular body which is formed continuously with the balloon-securing structure. For example, the shaft and balloon-securing structure may form a continuous tube, wherein a distal portion of the tube is axially split to permit balloon expansion therein. Thus, the shaft is in the form of a sleeve having a flexible conduit structure attached over a distal portion thereof. Alternatively, the tube can include an elastomeric region, mesh structure, enlarged (non-distensible) pouch, or the like, each of which permit internal balloon expansion.

For coronary applications, the proximal shaft structure will be designed to lie within a conventional guide catheter and may comprise a more flexible distal portion and a less flexible proximal portion. The more flexible distal portion will be sized to extend across the aortic arch, typically having a length from 10 cm to 25 cm. The less flexible proximal portion will be sufficiently long to extend through the femoral artery from a penetration in the groin to the aortic arch, typically being in the range from 80 cm to 120 cm. The flexible conduit structure will be sufficiently long to extend from a coronary ostium into the distal-most coronary vasculature, typically being from 10 cm to 20 cm. The more flexible distal portion of the proximal shaft structure will typically have a diameter in the range from 0.8 mm to 1.2 mm, while the less flexible proximal portion will have a diameter from 0.5 mm to 0.8 mm.

In a preferred embodiment, the more flexible distal portion of the proximal shaft structure will be an extruded organic polymeric material, formed from one of the materials described above, which is optionally braid- or coil-reinforced to enhance pushability and steerability. Usually, the less flexible proximal portion of the shaft will be formed from hypotube or a solid core wire. Alternatively, the less flexible proximal portion could be formed from an extruded organic polymeric material which is reinforced to a greater degree than the more flexible distal portion of the shaft. Optionally, a transition region may be provided between the flexible distal portion and the less flexible proximal portion of the shaft structure. It will be appreciated that direct joining of a hypotube or solid coil wire to an extruded organic polymeric material can result in a high stress connection which is subject to kinking and collapse. Such a transition region may be provided in a number of ways. For example, for braid- or coil-reinforced flexible portions of the shaft, the degree of reinforcement can be changed over its length so that the flexible portion is relatively stiff near the less flexible proximal portion of the shaft, with an increasing flexibility in the distal direction.

In a preferred embodiment, the transmission may be provided by selectively forming slots in the hypotube or wire which forms the less flexible proximal portion of the shaft. The hypotube or wire may be slotted using patterns that provide articulations between adjacent slotted segments, thus enhancing the flexibility of the distal most portion of the less flexible shaft portion. The selective use of slots allows the incorporation of a flexibility gradient, where the less flexible shaft portion is most flexible near its distal end, i.e. adjacent the more flexible shaft portion. As an alternative to discrete slots, a flexibility gradient may be provided by one or more spiral slot(s) where the spacing between adjacent turns of the spiral(s) decreases in the distal direction to enhance the flexibility of the most distal portions of the less flexible shaft portion.

In the case of a hypotube structure, where a continuous lumen is used for fluid delivery, the slotted portion of the shaft may be covered by a polymeric jacket, optionally being thermally formed or extruded over the hypotube. When formed or extruded, the polymeric material can be extended beyond the distal end of the hypotube to form the flexible distal portion of the shaft. The transition region of the shaft will typically have a length in the range of about 2 cm to 10 cm.

In addition or as an alternative to providing a flexibility gradient in the distal end of the hypotube, it may also be desirable to provide a tapered stylet which extends through the hypotube and into the proximal end of the flexible conduit structure. The stylet could replace the tether, described elsewhere, and would have the advantage that it is removable. Thus, the perfusion shunt device could be introduced with the stylet in place (providing enhanced column strength and kink resistance in the transition region), and then the stylet could be removed, leaving the hypotube lumen free for other purposes, such as fluid agent delivery.

In a particularly preferred embodiment, the proximal shaft structure includes a continuous lumen along its entire length so that fluids may be introduced from the proximal end of the perfusion shunt device into the perfusion path(s) or lumen(s) in order to provide for introduction of therapeutic agents, contrast media, or other liquid compositions. In the case where the perfusion shunt device includes two or more parallel lumens, the single lumen of the proximal shaft structure may be fluidly coupled to the doubled perfusion lumen by an internal bifurcation in the shaft.

Optionally, the flexible conduit structure may be attached to the proximal shaft structure using a tether running at least partially along the length of the perfusion shunt device. In an exemplary embodiment, the tether will be secured within a lumen of the flexible conduit structure and run through or over both the more flexible distal portion and the less flexible proximal portion of the shaft structure. The tether serves both to enhance the pushability (column strength) of the perfusion shunt device as well as helping to prevent accidental loss of the device components, particularly by breakage at the junctions between the flexible catheter structure and the proximal shaft structure and/or between the distal and proximal portions of the proximal shaft structure.

Referring now to FIG. 1, a first embodiment of the perfusion shunt device of the present invention will be described. The perfusion shunt device 10 comprises a flexible conduit structure 12, a balloon-securing sleeve 14, and a proximal shaft 16. The balloon-securing sleeve 14 has an open port 18 at its distal end and a shaft anchor structure 20 at its proximal end. The proximal shaft 16, which is in the form of a narrow-diameter rod or hypotube, is secured directly to the proximal end of the flexible conduit structure 12 and passes through a ring structure 22 on the anchor 20.

The flexible conduit structure 12 comprises a pair of lumens 24 extending axially from its distal end to proximal end. Each lumen 24 includes a plurality of axially spaced-apart blood perfusion ports 26. The construction of such a dual-lumen flexible conduit structure is described in more detail in copending application Ser. No. 08/222,143, the full disclosure of which has been previously incorporated herein by reference.

Figure 4:
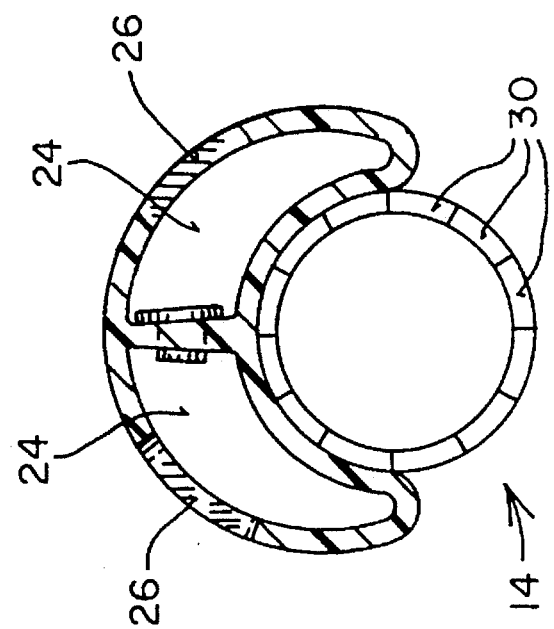
FIG. 4 is a cross-sectional view of the catheter of FIG. 1, shown in a non-expanded configuration.

Referring now to FIGS. 1–5, the balloon-securing sleeve 14 is axially split into a number of discrete segments 30, as best observed in FIGS. 4 and 5. The axially split region of the sleeve 14 will be sufficiently long to accommodate a conventional balloon B on a balloon angioplasty catheter C (FIG. 2). The balloon-securing sleeve 14 and flexible conduit structure 12 are separate, discrete components which are attached to each other only at attachment points 34 and 36 (FIGS. 2 and 3), which are disposed distally of and proximally to the balloon-receiving region of sleeve 14, respectively. Thus, when the balloon B is expanded within the sleeve 14, as illustrated in FIG. 3, the distal and proximal regions of the sleeve 14 over the balloon will be formed into smooth curves, as illustrated. Such smooth curves help to expose the ports 26 upstream and downstream of the balloon to blood flowing closer to the center of the blood vessel being treated.

Referring now to FIG. 6A, a perfusion shunt device 40, similar in most respects to device 10, is illustrated. The device 40 is identical, except that an elastomeric segment 42 is provided in place of the axially split portion of sleeve 14'. All other numbering in FIG. 6A is identical to that used in FIGS. 1–5.

Another perfusion shunt device 44 having a radially expansible mesh section 46 in sleeve 14" is illustrated in FIG. 6B. All other details of construction of device 44 may be identical to those described for FIG. 1. Thus, all other reference numbers used for identifying like components are identical.

Yet another perfusion shunt device 45 having a radially expansible pouch 47 formed from a non-compliant material, such as polyethyleneterephthalate (PET), is illustrated in FIG. 6C. The pouch 47 will be folded (as illustrated in FIG. 6C) prior to internal expansion of a balloon. The pouch 47 will usually be sized smaller than the balloon with which it is to be used so that the pouch will constrain radial expansion of the balloon. In that way, the same balloon which has been used in an angioplasty procedure may be reused in the subsequent perfusion procedure with minimum risk of over stretching the blood vessel. It will be appreciated that presence of the flexible conduit 12 over the balloon could increase the effective balloon diameter to some extent. Should an increase in effective expansion diameter be desired, the balloon can be further inflated to distend the pouch and provide the desired enlargement. Alternatively, an increase in effective expansion diameter can be achieved by deploying a different perfusion shunt device having a larger effective expansion envelope, as described above.

Referring now to FIG. 7, yet another embodiment of the perfusion shunt device of the present invention will be described. Perfusion shunt device 50 includes a flexible conduit structure 52 which is analogous to structure 12 in FIG. 1. The flexible conduit structure 52, however, is not attached to a proximal shaft. Instead, perfusion shunt device 50 employs an elongate sleeve 54 which acts as both a balloon-securing sleeve and a proximal shaft structure. A balloon-securing region 56 within the sleeve 54 may comprise an axially slit region (wherein the sleeve may be composed of a non-elastomeric material) as illustrated, or may comprise any of the other balloon containment cages described previously. A conventional balloon catheter C (shown in broken line) is received within a lumen 58 of the sleeve 54 which extends the entire distance from the distal port 60 to a proximal housing 62 of the device. It will be appreciated that the flexible conduit structure 52 is attached to the sleeve 54 only at locations distal to and proximal of the expansible region 56 of sleeve 54 which receives the balloon on catheter C.

Referring now to FIGS. 8 and 9, yet another embodiment of the perfusion device shunt device will be described. Perfusion shunt device 70 is similar in most respects to device 10 of FIGS. 1–5, except that the flexible conduit structure 72 provides open, axial channels 74 in place of the closed lumens 24 in the conduit structure 12. Balloon-securing sleeve 78 and axial rod 80 may be formed substantially identical to the corresponding components in device 10.

Referring now to FIGS. 10–13, still another embodiment of the perfusion shunt device of the present invention will be described. Perfusion shunt device 90 comprises a flexible catheter structure 92 which is similar in most respects to structure 12 of FIG. 1. Device 90, however, does not employ an expansible cage or sleeve structure, as with all previous embodiments. Instead, device 92 employs discrete distal anchor 94, which receives the distal end of a balloon catheter C, as best seen in FIG. 11. Preferably, device 90 further comprises proximal anchor structure 96, which is located near the proximal end of the conduit structure 92. A proximal rod 98 is attached directly to the conduit structure 92.

In use, the perfusion shunt device 90 will be attached over balloon B of the catheter C, with proximal anchor 96 at a location proximally spaced-apart from the balloon. The balloon B is inflated, as illustrated in FIG. 13, with the desired arcuate profiles of the conduit structure 92 being achieved.

Any of the perfusion shunt devices described herein may be used by loading them onto a balloon catheter so that the flexible conduit structure lies over the balloon while the catheter is outside the body. Indeed, the device 90 of FIGS. 10–13 and the device which does not include a proximal shaft structure (not illustrated) must be loaded on the catheter outside the body. The other embodiments must be loaded over the distal end of the balloon catheter while the balloon catheter is outside the body. The other embodiments, however, permit the flexible conduit structure to be distally advanced and proximally withdrawn relative to balloon of the balloon catheter while the catheter and the shunt device both remain within the blood vessel, which ability is not available with device 90.

Referring now to FIGS. 14–21, another embodiment of the perfusion shunt device of the present invention will be described. Perfusion shunt device 100 comprises a flexible conduit structure 102 and a proximal shaft structure 104 including both a more flexible distal section 106 and a less flexible proximal section 108. The flexible conduit structure 102 is formed as a single extrusion, typically from polyethyleneterephthalate, having four lumens therethrough. The first lumen 110 includes non-distensible pouch structure 112 which defines a balloon-receiving cavity, as described in more detail hereinafter. The second lumen 114 and third lumen 116 define the blood perfusion paths through the conduit structure 102. A fourth lumen 118 receives a tether 120 which runs the length of the perfusion shunt device.100. Alternatively, the fourth lumen 118 may be filled with polymeric or other materials to enhance the strength of the conduit structure 102, particularly so that perfusion lumens 114 and 116 are resistant to collapse. In some cases, it may also desirable to locate radiopaque markers within the fourth lumen 118, as described in more detail below.

A plurality of axially spaced-apart perfusion ports 122 are formed in each of the perfusion lumens 114 and 116, as best observed in FIG. 16. In many cases, it will be desirable to provide a greater number of perfusion ports 122 over the distal portion of the flexible conduit structure 102, particularly in the region of the balloon pouch 112, as shown in FIG. 16. Additional ports 122, however, should be provided along the entire length of the flexible conduit structure so as to assure that sufficient blood will be able to enter the perfusion lumens 114 and 116 should some parts become obstructed, in order to provide the desired perfusion flow.

Figure 18:
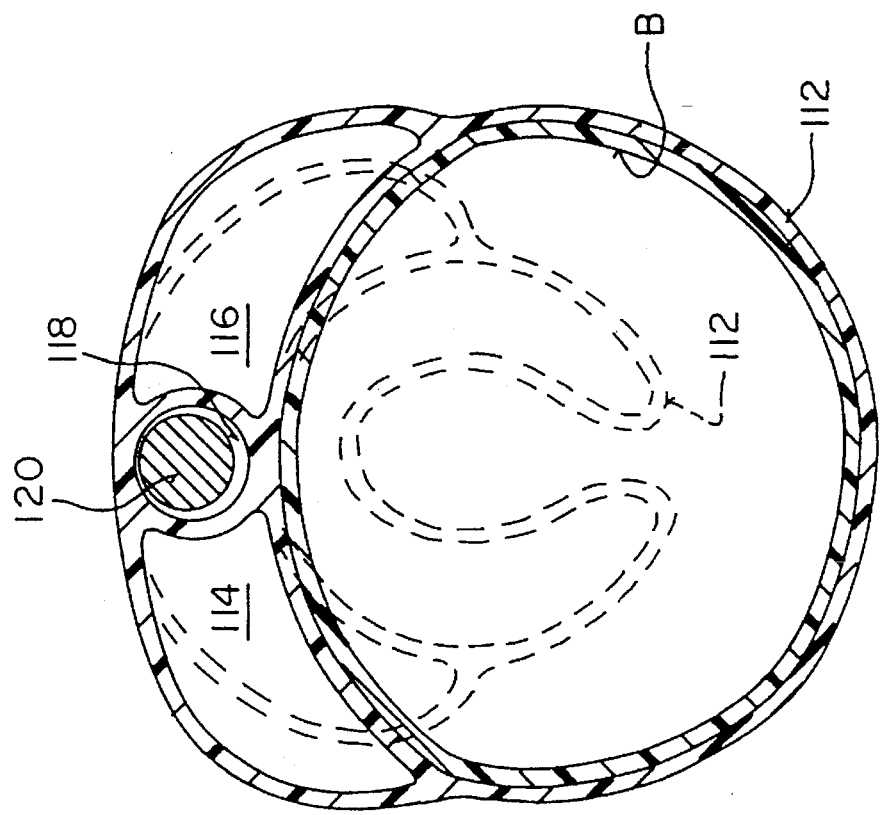
FIG. 18 is a cross-sectional view taken along line 18—18 of FIG. 15.
Figure 17:
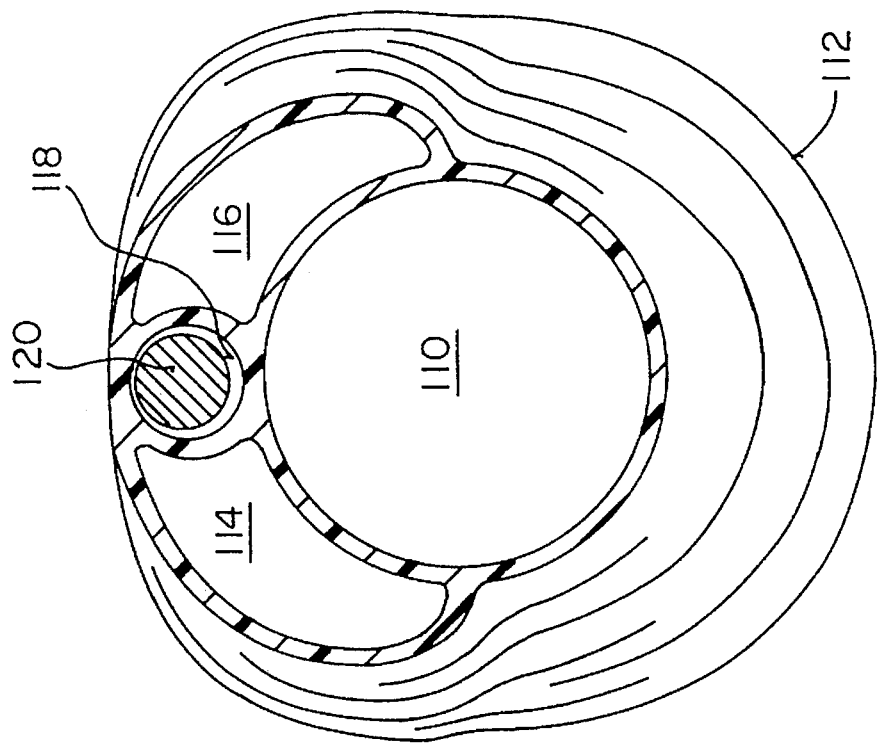
FIG. 17 is a cross-sectional view taken along line 17—17 of FIG. 15.

The more flexible distal section 106 will be formed as a tubular extrusion, having a primary lumen 130 (FIG. 19) for permitting the infusion of fluids, and a second lumen 132 which receives the tether 120 therethrough. In this way, the tether 120 continues uninterruptedly from lumen 132 in the more flexible distal section 106 (FIG. 19) into and through lumen 118 in the flexible conduit structure (FIG. 17 and 18). Alternatively, the tether can float freely in lumen 130 and then enter lumen 118 following the transition from the more flexible distal section 106 to the flexible conduit structure 102.

As shown in FIGS. 14–22, the flexible conduit structure 102 perfusion shunt device includes two perfusion lumens. The transition from the more flexible distal section 106 of the proximal shaft structure to the flexible conduit structure 102 will incorporate an internally ducted bifurcation (not shown) to allow fluids in the single lumen 130 to flow into lumens 114 and 116 of the flexible conduit structure 102.

Figure 20:
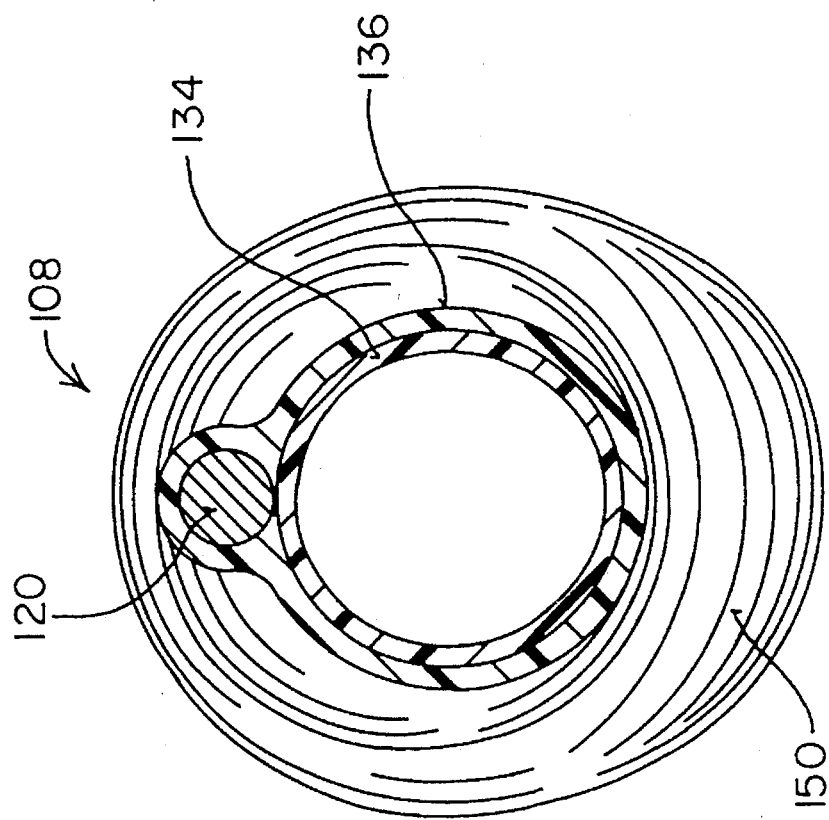
FIG. 20 is a cross-sectional view taken along line 20—20 of FIG. 15.
Figure 19:
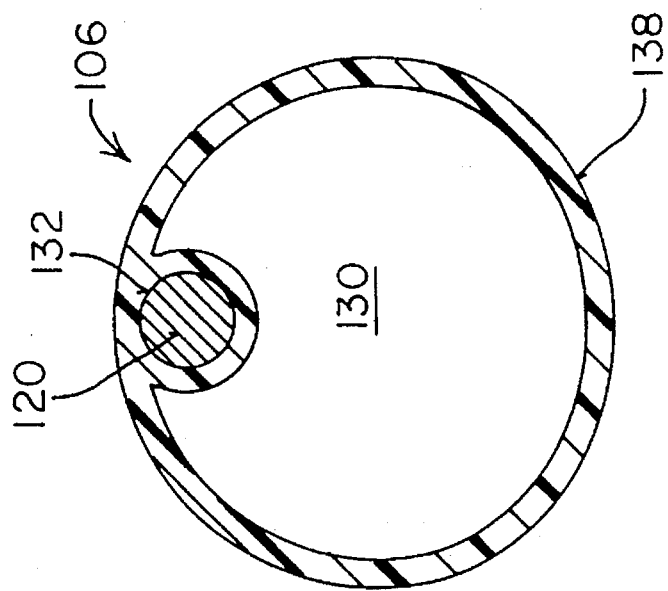
FIG. 19 is a cross-sectional view taken along line 19—19 of FIG. 15.

The less flexible proximal section 108 of the perfusion shunt device 100 is typically formed from hypotube 134 (FIG. 20). The tether 120 may run parallel to the hypotube 134, usually being attached thereto, for example by a heat shrinkable sheath thereover. Conveniently, the sheath attaching tether to hypotube 134 may be formed by extending the extrusion of which forms the more flexible distal section 106 proximally over at least a portion of the less flexible proximal section 108. (Such an extension 138 is shown in FIG. 20).

Preferably, the more flexible distal portion 106 and less flexible proximal portion 108 of the proximal shaft 104 will be joined with a transition region which increases in flexibility in the distal direction. Preferably, such a transition region will have a length from 2 cm to 10 cm (often about 5 cm) and can be formed by modifying the distal end of hypotube 108, e.g. by providing spaced-apart slots which facilitate articulation and decrease the bending stiffness. By properly selecting the spacing between adjacent slots, the structure will possess a desired bending stiffness gradient over the transition region, where the stiffness at the distal end of the transition region approaches that of the flexible distal section and the stiffness at the proximal end of the transition region closely matches that of the less flexible proximal section. The transition region could also be provided by one or more spiral slots formed in the hypotube where the pitch of the spiral decreases (i.e., the spacing between adjacent turns of the spiral decreases) in the distal direction to create the desired stiffness gradient.

An exemplary transition region is illustrated in FIG. 21, where a plurality of H-shaped slots are cut into the hypotube 108 at preselected spacings. Distal end 109 of the hypotube 108 will be attached to the proximal end of the more flexible distal region 106 of shaft 104. As can be seen, the H-shaped slots 111 are spaced together more closely near the distal end 109 than over the proximal portions of the hypotube 108.

As illustrated in cross-section in FIG. 21A, the opposed H-shaped slots 111 create a pair of diametrically opposed beams 113 joining adjacent hypotube sections 115. The beams 113 permit flexing of the hypotube 108 about a transverse axis passing through the center of the opposed beams, as illustrated in FIG. 21B. By then rotationally offsetting the adjacent beam pairs 111, usually by an angle of 90° as seen in FIG. 21, the hypotube 108 will be able to flex in either orthogonal direction or any other angular combination thereof. As described previously, when the lumen 117 of the hypotube 108 is intended to deliver fluids to the flexible conduit structure 102, the tube may be covered with a jacket or sleeve formed from a compliant material, usually an organic polymer. Preferably, the jacket will be a continuation of the polymer used to form the more flexible distal section 106 of the shaft 104.

Figure 21C:
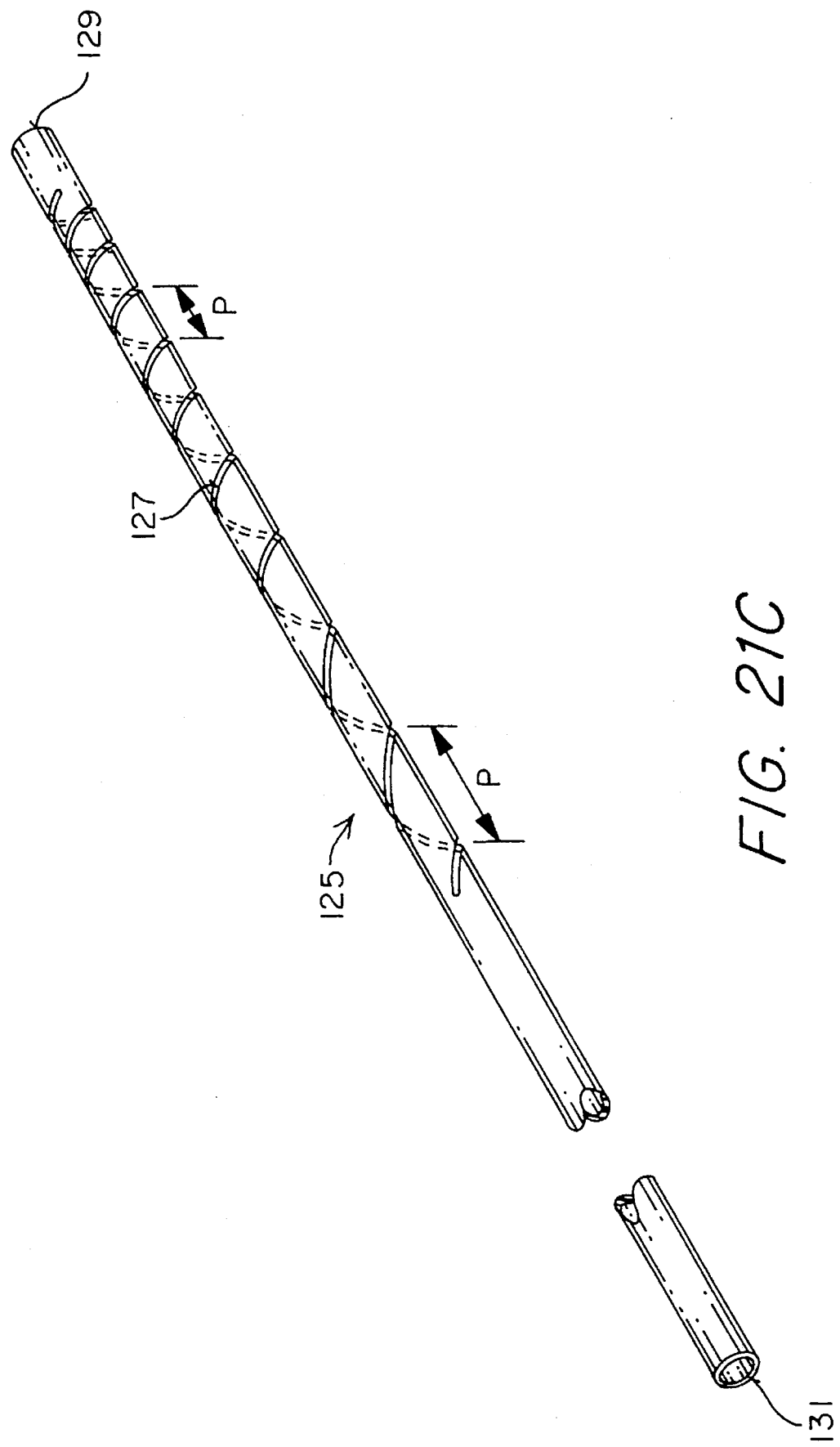
FIG. 21C is a detailed view of a tubular member having a spiral slot that provides controlled flexibility in a more rigid proximal section of the proximal shaft structure.

A preferred transition region is illustrated in FIG. 21C, where hypotube 125 has a single, continuous spiral slot 127 formed from near a distal end 129 toward a proximal end 131 thereof. The distal end 129 will be attached to the proximal end of the more flexible distal region 106 of shaft 104, as shown previously. The pitch p between adjacent turns of the spiral slot 127 decreases in the distal direction in order to provide enhanced flexibility and a desired flexibility gradient in the distal direction.

A proximal connector, typically a standard male luer lock, is provided at the proximal end of the hypotube 34 to permit fluid connection of the perfusion shunt device to a conventional fluid source, such as source of therapeutic agent, contrast media, perfusion fluid, flushing fluid, or the like, such as a heparinized saline flushing fluid.

The non-distensible pouch 112 is best illustrated in FIG. 18. The pouch 112 is shown in its non-expanded configuration in broken line. Pouch 112 will remain in its undeployed configuration until a balloon B is inflated therein, as shown in full line in FIG. 18. It can be seen that expansion of balloon B opens the perfusion lumens 114 and 116 in a manner similar to that described above with reference to FIGS. 4 and 5. Upon deployment, perfusion lumens 114 and 116 open up, as illustrated in FIG. 18, which provides an enhanced available perfusion lumen area, as described in detail in pending application Ser. No. 08/305,250, the disclosure of which has previously been incorporated herein by reference. Usually, the perimeter of pouch 112 when fully deployed will be selected to be slightly smaller than the diameter of balloon B which is being expanded therein. In this way, the expanded envelope size dimension of the perfusion shunt device in the region of the pouch can be limited to be equal to that of angioplasty balloon. This is an advantage since it permits subsequent use of the same angioplasty balloon which has been used for an initial angioplasty treatment in conjunction with the perfusion shunt device. That is, the additional size of the perfusion shunt device will not incrementally expand the blood vessel, reducing the chance of injury to the blood vessel. Alternatively, the expanded envelope size of the perfusion shunt device can be chosen to correspond to a conventional angioplasty balloon having an outer diameter which is slightly greater than that of the angioplasty balloon initially employed in a procedure, typically being from 0.25 mm to 0.50 mm larger. The slightly larger size is sometimes beneficial when the perfusion shunt device is being used to "tack up" a dissection in the treated blood vessel.

Figure 14:
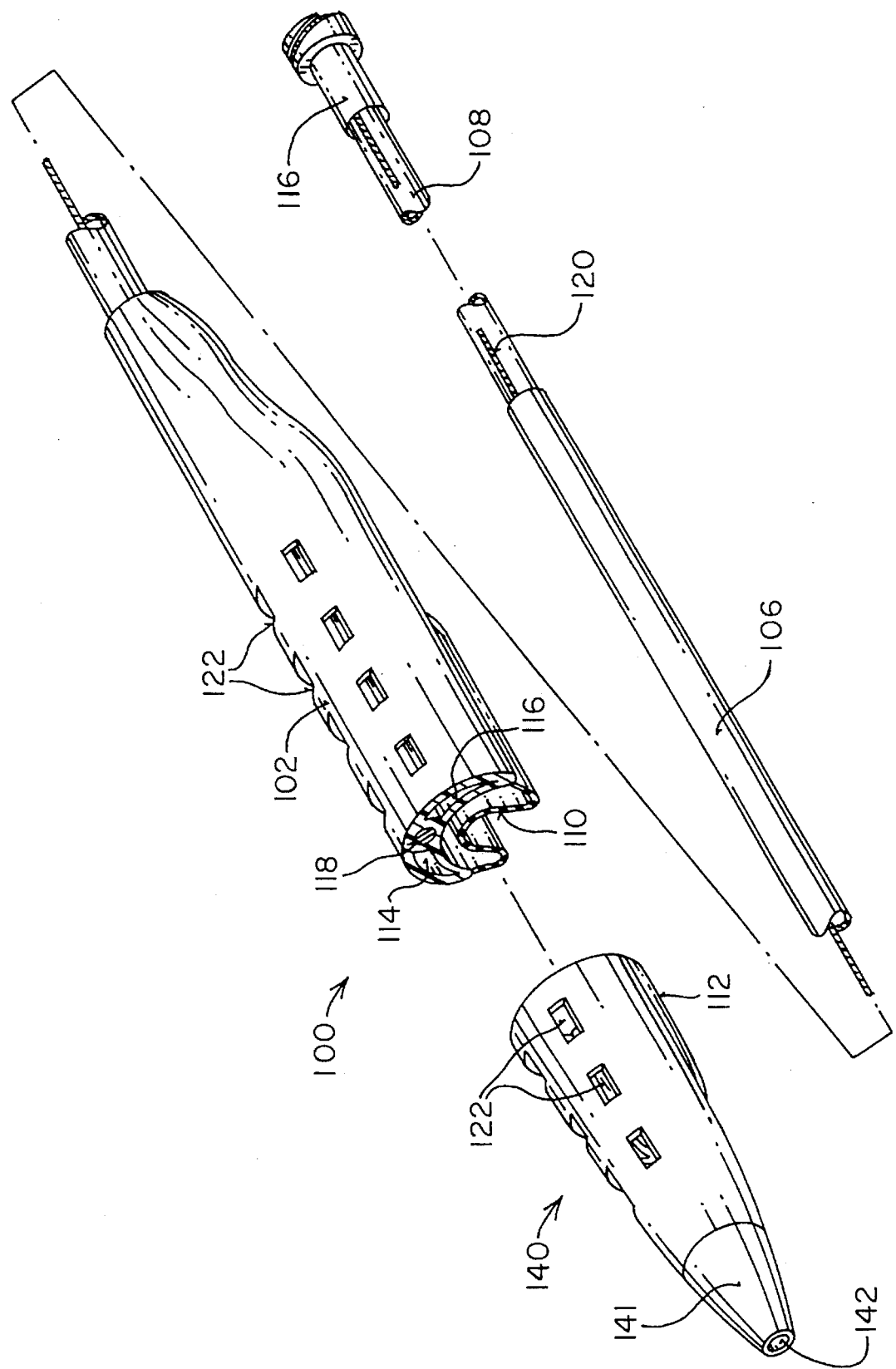
FIG. 14 is a perspective view of yet another alternative embodiment of a perfusion shunt device constructed in accordance with the principles of the present invention and including a non-distensible pouch which is formed integrally along a flexible conduit structure.

The perfusion shunt device 100 is shown to have a tapered distal tip region (FIG. 14). The tapered distal region 140 has a port 142 which is sized to receive a conventional guidewire, typically having a diameter in the range from about 0.25 mm to 0.5 mm. With such a tapered distal region 140, the angioplasty balloon can pass only through a balloon-introduction port 150 (FIG. 15) located at the proximal end of the flexible conduit structure 102. It will be appreciated that in order to use such a structure following an angioplasty procedure, the angioplasty balloon B must first be withdrawn entirely from the patient. The angioplasty balloon can then be introduced through the port 150, and the perfusion shunt device 100 and angioplasty balloon catheter reintroduced together over a guidewire to the treatment site.

A distal tip 141 of the tapered distal region 140 can alternatively be made to be expansible so that the distal port 142 can be enlarged to a diameter in the range from 1 mm to 1.7 mm for receiving a balloon angioplasty catheter. The port 142 could also be with a fixed diameter in the range from 1 mm to 1.7 mm to accommodate the distal end of an angioplasty balloon as shown in FIG. 22 discussed below.

Figure 15A:
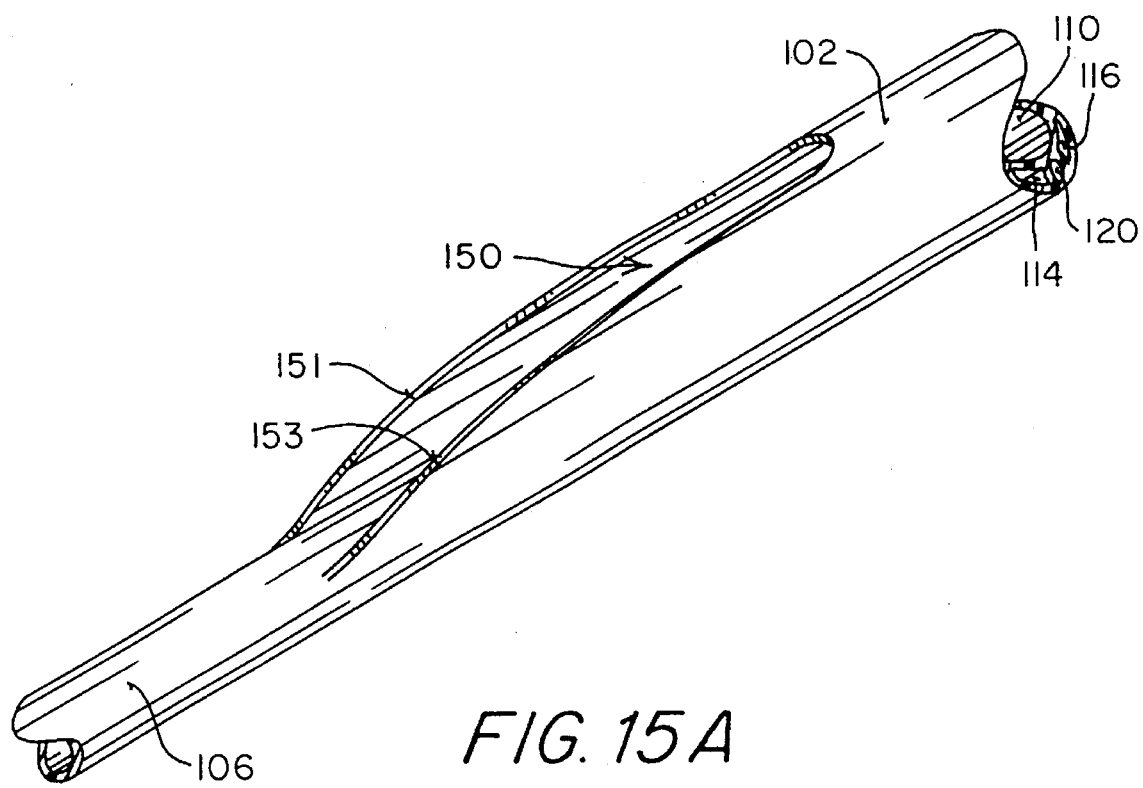
FIG. 15A is a detailed view of the balloon introduction port of the perfusion shunt device of FIGS. 14 and 15.
Figure 15B:
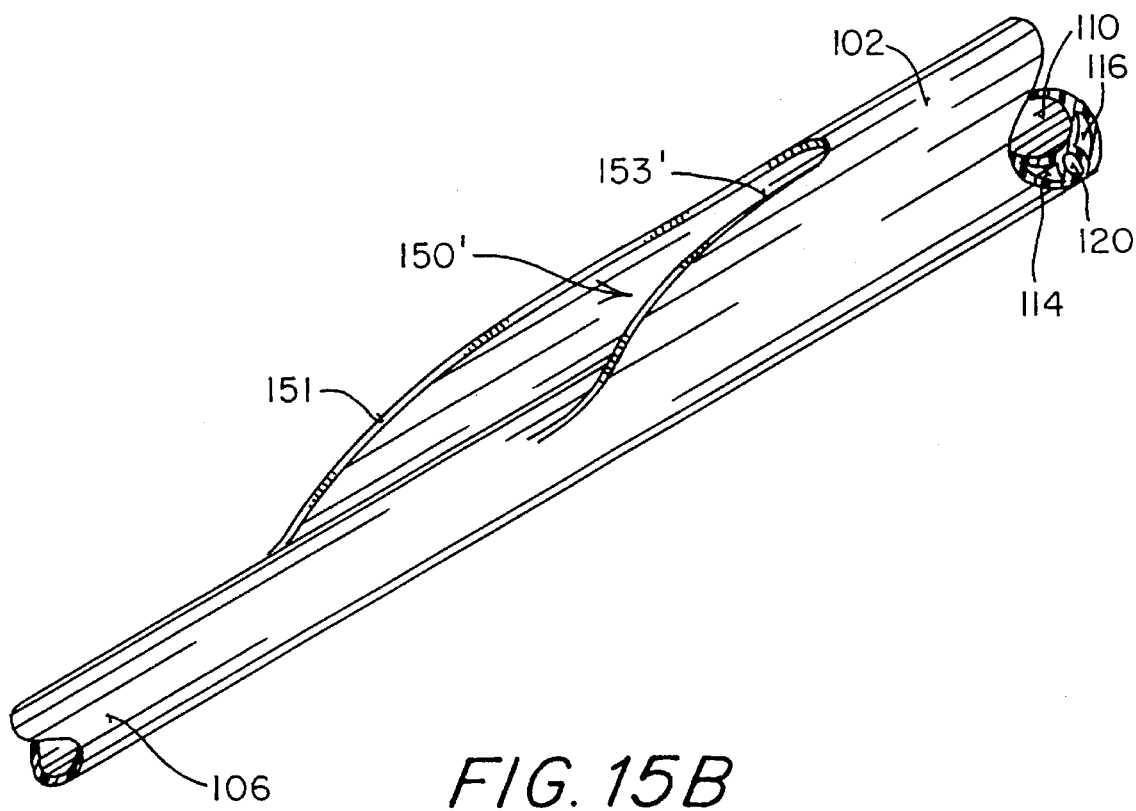
FIG. 15B is an alternative embodiment of a balloon introduction port for the perfusion shunt device of FIGS. 14 and 15.

The balloon introduction port 150 is illustrated in more detail in FIG. 15A. The introduction port 150 is defined by a pair of generally parallel walls 151 and 153 which define an elongated channel for receiving and refolding the balloon catheter as it is passed distally into the lumen 110. A modified entry port 150' as illustrated in FIG. 15B. The introduction port 150' is similar to introduction port 150, except that wall 153' has been shortened so that it does not extend as far as wall 151 in the proximal direction. The advantage of port 150 and the design of port 150' is that a previously inflated balloon (which will typically have a "winged" or flattened shape when deflated with a vacuum drawn through the inflation lumen) may be introduced into the port 105 or 150' and be properly folded as it passes through the channel. It has been found that the use of one axially shorter wall is even more effective in folding the deflated balloon neatly over in what can be called a "propeller" fold.

Figure 22:
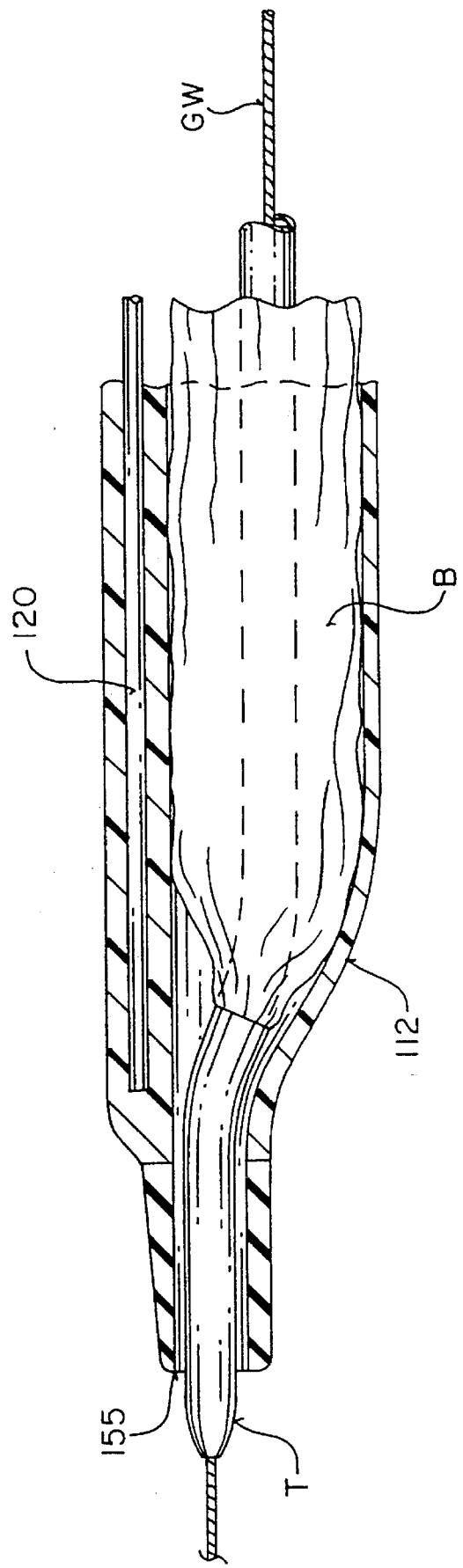
FIG. 22 is a cross-sectional view of a distal portion of a perfusion shunt device similar to that illustrated in FIGS. 14–21, except that the distal tip has been enlarged to permit passage of a balloon catheter therethrough.

The distal end of the perfusion shunt device 100, however, can be formed to have a larger distal port 155 to permit passage of the distal tip T of the balloon catheter B, as illustrated in FIG. 22. Optionally, the tip surrounding the distal port 155 can be formed from a soft (low durometer) material. Such a soft tip is advantageous both because it is atraumatic to the arterial tissue and also because it can distend as necessary to accommodate the balloon tip T. The remaining portions of the perfusion shunt device illustrated in FIG. 22 are generally similar to those described for perfusion shunt device 100, and will have the same reference numerals. As can be seen, the distal tip T of balloon catheter B can extend through the distal port 155 of the perfusion shunt device. Balloon B can be inflated within the balloon-receiving cavity of pouch 112. Both the balloon catheter and the perfusion shunt device are received over a guidewire GW, in a conventional manner. With the larger distal port 155, the perfusion shunt device can be withdrawn proximally over the balloon B of the angioplasty catheter to permit simultaneous introduction of the combination. The balloon B can then be selectively advanced beyond the distal port 155 when it is desired to perform angioplasty.

The distal port 155 could be made even larger to accommodate a folded distal portion of the balloon B on the balloon catheter (not shown). The length of the balloon-receiving cavity in pouch 112 will then be shortened to fully contain the balloon B when expanded. The short projection, typically 1 mm to 1 cm, of the distal tip of the balloon beyond the perfusion shunt device 100 is advantageous in that it provides an extension of the tapered end of the shunt device.

Figure 23:
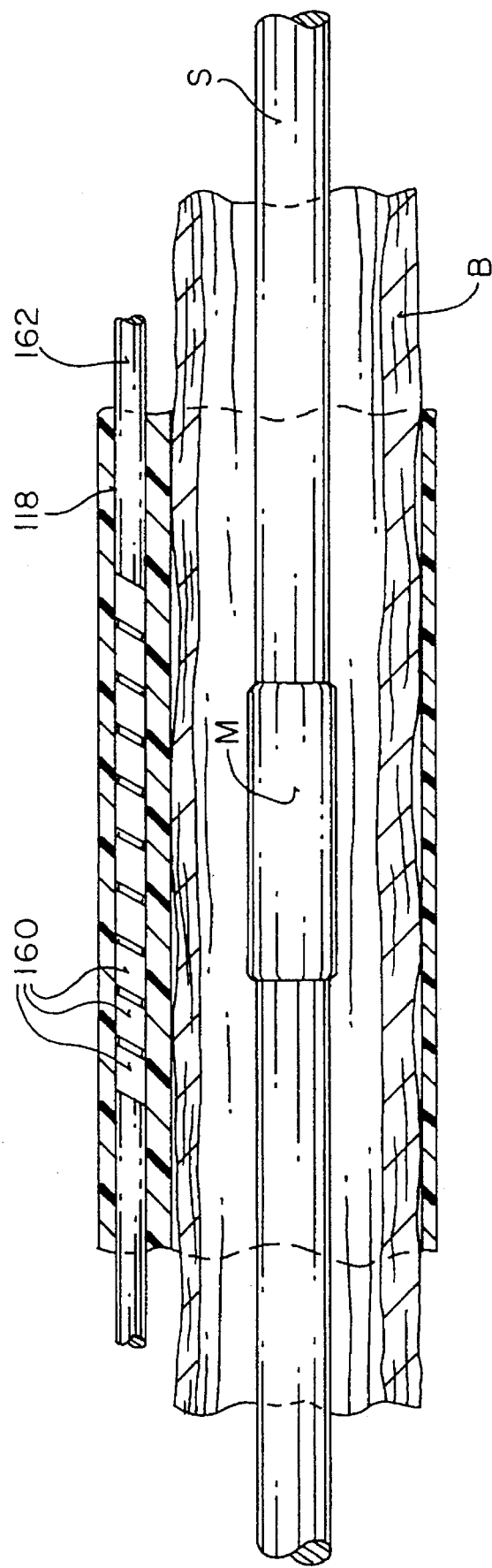
FIG. 23 is a cross-sectional view of the catheter of FIGS. 14–21 illustrating a helical, radiopaque marker and the alignment of such marker with a radiopaque marker on a balloon catheter.

A preferred marker system for the perfusion shunt device 100 is illustrated in FIG. 23. The marker comprises a helical structure 160 disposed within the fourth lumen 118, optionally over a polymeric rod 162. The marker 160 will be longer than a conventional marker M located within balloon B on the shaft S of the angioplasty balloon catheter. As the marker 160 will be longer than the conventional marker M, and typically be narrower, the treating physician can properly locate the perfusion shunt device over the angioplasty balloon by centering the marker 160 over the balloon catheter marker M while viewing the treatment region fluoroscopically. Such proper alignment will result in the balloon B being properly located within the balloon-receiving cavity of pouch 112. Optionally, it will be possible to employ a pair of spaced-apart markers on the perfusion shunt device where proper alignment is achieved when the single marker M is aligned between the spaced-apart markers, as disclosed in copending application Ser. No. 08/305,250, the disclosure of which has previously been incorporated herein by reference.

An alternative embodiment 200 of the perfusion shunt device of the present invention is illustrated in FIGS. 24–31. Perfusion shunt device 200 includes design features intended to increase the available perfusion lumen area and to reduce the likelihood that the flexible conduit structure will kink when bent during use, e.g. when being passed through tortuous regions of the vasculature. The design features which achieve these objectives will be discussed in more detail below.

The perfusion shunt device 200 includes a flexible conduit structure 202 and a proximal shaft structure 204. The flexible conduit structure 202 includes both a distal balloon-receiving section 206 and a proximal blood-uptake section 208 having blood uptake ports 209. The proximal shaft section 204 includes both a more flexible distal section 210 and a less flexible proximal section 212.

Referring in particular to FIG. 27, an increase in the cross-sectional area of perfusion lumens 216 and 218 is achieved primarily by reducing the area of a third lumen 220 which receives the shaft of the angioplasty balloon B in a manner analogous to the third lumen 110 of the embodiment of FIGS. 14–22.

The distal balloon-receiving section 206 of the flexible conduit structure 202 is strengthened against kinking by reducing the number of blood perfusion ports therein. In particular, only a pair of large distal perfusion ports 224 will be provided only at the distal end of section 206, significantly enhancing the strength and kink-resistance of the remaining portion of that section. In some cases, it may also be desirable to increase the wall thickness surrounding the perfusion lumens 216 and 218, typically to about 0.1 mm.

Other design features of the perfusion shunt device 200 within the distal balloon-receiving section 206 of the flexible conduit structure 202 include a structure where the distal tip 228 is radially centered with respect to the more proximal regions of section 206. Such geometry increases the likelihood that distal perfusion ports 224 will not be occluded by the blood vessel wall when a balloon is expanded within the balloon-receiving section 206. Preferably, the distal tip 228 will be formed from a soft (low-durometer) material. Such a soft structure both decreases the likelihood of traumatic injury to the arterial wall during introduction of the perfusion shunt device 200 and permits the tip to resiliently yield when the distal end of the balloon catheter B is passed therethrough. The balloon catheter B is illustrated in broken line in FIG. 24.

Figure 30:
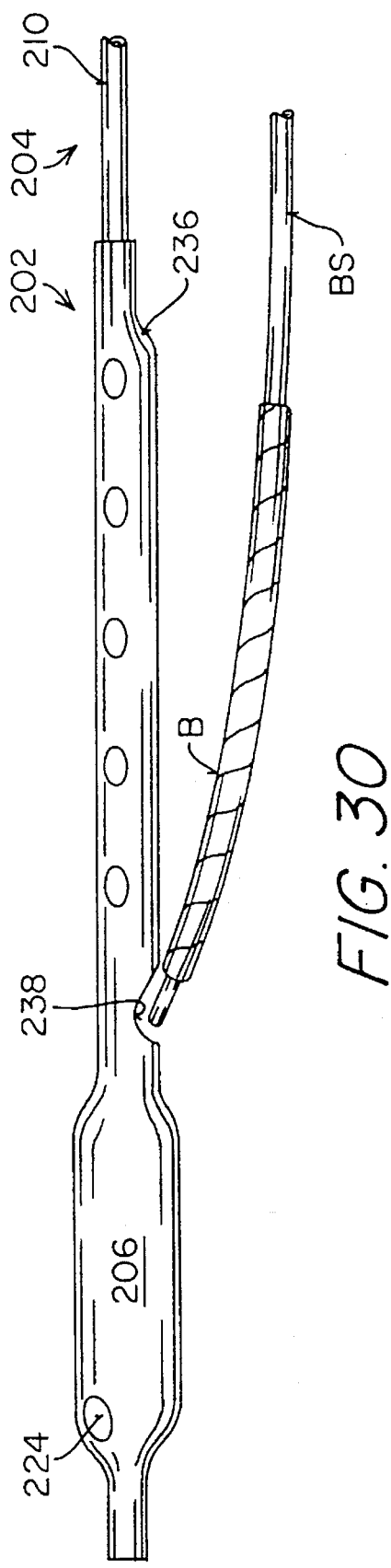
FIGS. 30 and 31 illustrate the introduction of a balloon angioplasty catheter into the perfusion shunt device of FIG. 24.

Referring now in particular to FIGS. 28 and 29, the proximal blood-uptake section 208 at the proximal shaft structure 204 will be a dual-lumen extrusion comprising a single perfusion lumen 230 and a balloon catheter shaft-receiving lumen 232. The cross-sectional area of the balloon catheter shaft-receiving lumen 232 can be greatly reduced by incorporating an axial split 234 along its entire length. It will be appreciated when a balloon catheter B is in place as illustrated in broken line in FIG. 24, only the shaft portion BS of the balloon catheter B will be within the lumen 232. As the shaft BS has a diameter which can be substantially less than that of the balloon region of the catheter B, the cross-sectional area required is less than that needed to pass the balloon. By splitting the lumen 232, the balloon portion of the balloon catheter B can either be passed through a proximal port 236, with the axial split 234 temporarily opening to permit passage of the larger-diameter balloon, or can be introduced through an intermediate port 238, with the balloon shaft BS subsequently being pressed through the axial split 234 as illustrated in FIGS. 30 and 31.

The loss of structural support from the fourth lumen (and the tether or other structure which may be located therein) is at least partially compensated for by the ability to increase the wall thickness surrounding the lumen. By reducing the total cross-sectional area of the two-lumen section 208 relative to the four-lumen section 206, the walls of the section 208 can be made thicker and thus more kink resistant, particularly where the wall is weakened by the presence of blood uptake ports 209. Equally important, a single lumen for blood uptake reduces the hydraulic pressure drop in comparison to the use of multiple lumens. Additionally, the absence of a septum in section 202 permits unimpeded flow into and out of the uptake ports 209, even if ports on one side of the section 202 are blocked or impeded.

Figure 31:
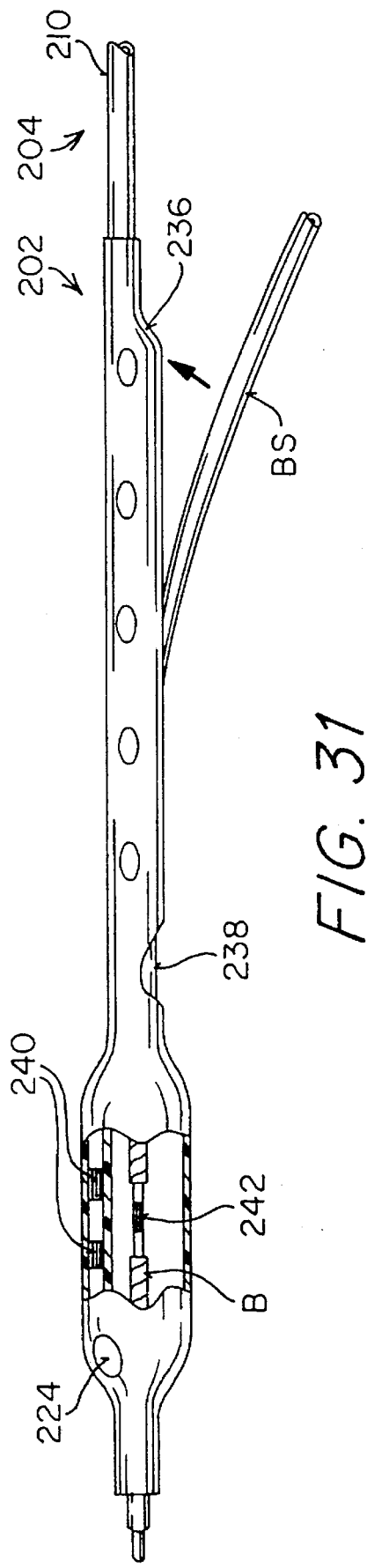

Referring now in particular to FIG. 31, a pair of spaced-apart radiopaque markers 240 can be provided within the lumen 222 of the distal balloon-receiving section 206 of the flexible conduit structure 202. The axial position of the spaced-apart markers 240 is selected so that they will straddle, i.e. lie on opposite sides of a single marker 242 present on the balloon catheter B. It will be appreciated that conventional balloon catheters commonly include at least a single marker centered within the balloon structure itself. Based on the known dimensions of the conventional balloon catheter B and the desired location of the balloon catheter tip relative to the tip of the perfusion shunt, the markers 240 can be appropriately placed so that the balloon will lie in the desired axial position within the balloon-receiving section 206 when aligned.

Referring now to FIGS. 32 and 33, an alternative design allowing a reduced cross-sectional area of the balloon-catheter-receiving lumen in a proximal blood-uptake section of a perfusion shunt device 300 will be described. Perfusion shunt device 300 includes a distal balloon-receiving section 302 (similar to that incorporated in device 200 of FIGS. 24–31) and a proximal blood-uptake section 304. Instead of incorporating a single axial split, as with blood-uptake section 208 in catheter 200, the blood-uptake section 304 will include a plurality of axially and circumferentially offset splits 310 which provide a readily expansible web structure to permit easy passage of the enlarged balloon portion of a balloon catheter B, as shown in FIG. 33. Balloon catheter B passes into introduction port 320, through the blood-uptake section 304 (where the splits 310 are temporarily opened to allowed passage of the enlarge balloon region of the catheter B), and eventually into the balloon-receiving section 302 where the balloon can be expanded as described previously. After the balloon has reached the balloon-receiving section 302, the balloon shaft BS will remain in the blood-uptake section 304, permitting the section 304 to collapse back to its smaller profile configuration with the splits closed.

Figure 34:
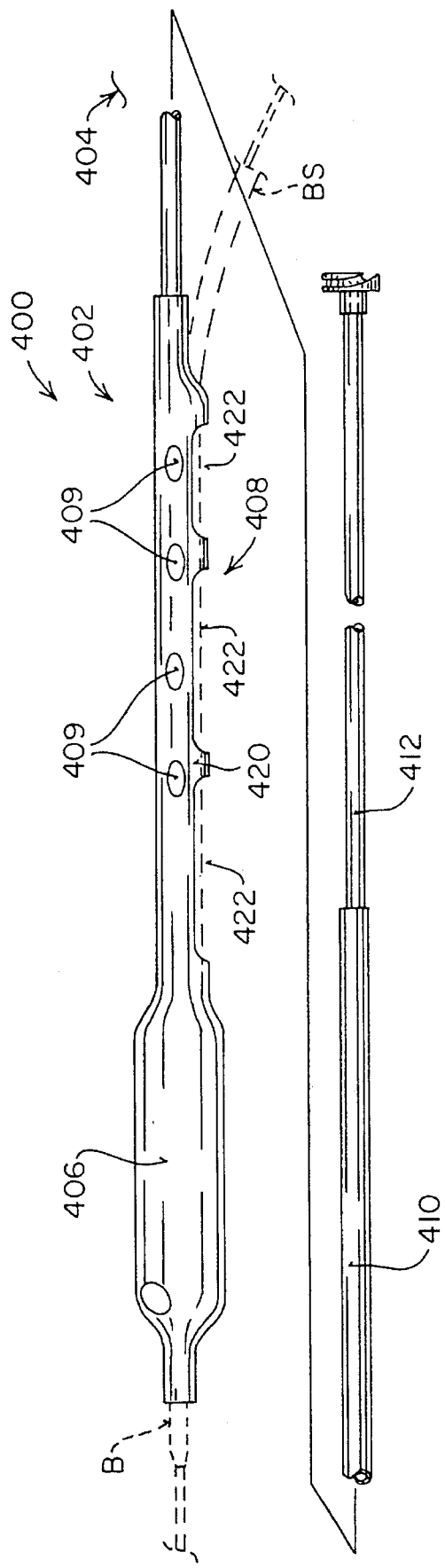
FIG. 34 is a side, elevational view of yet another alternative embodiment of a perfusion shunt device constructed in accordance with the principles of the present invention.

Referring now to FIG. 34, another alternative design for allowing a reduced cross-sectional area of the balloon-catheter-receiving lumen in a proximal blood-uptake section of a perfusion shunt device 400 is shown. Perfusion shunt device 400 includes a flexible conduit structure 402 and proximal shaft structure 404. The flexible conduit structure includes both a distal balloon-receiving section 406 and a proximal blood-uptake section 408 having blood uptake ports 409. The proximal shaft section 404 includes both a more flexible distal section 410 and a less flexible proximal section 412. As described thus far, the perfusion shunt device 400 is similar to device 200 described in connection with FIGS. 24–31 above.

Perfusion shunt device 400 differs from device 200 in the manner in which a third, balloon catheter receiving lumen 420 is formed in the proximal blood-uptake section 408 of the flexible conduit structure 402. Instead of a split lumen 232 (FIGS. 24 and 29), lumen 420 is cut-out in three sections 422 to facilitate entry and passage of balloon catheter B with catheter shaft BS finally being received in lumen 420, as shown in broken line in FIG. 34.

Although the foregoing invention has been described in some detail by way of illustration and example, for purposes of clarity of understanding, it will be obvious that certain changes and modifications may be practiced within the scope of the appended claims.

What is claimed is:

1. A perfusion shunt device for use in combination with an angioplasty balloon catheter, said device comprising:

a flexible conduit structure having a proximal end, a distal end, and a blood perfusion path extending axially over at least a portion of the conduit structure; and means on the conduit structure for removably securing said conduit structure over the angioplasty balloon of the catheter.

2. A perfusion shunt device as in claim 1, wherein the flexible conduit structure includes at least a balloon-receiving lumen and two perfusion lumens along its entire length.

3. A perfusion shunt device as in claim 1, wherein the flexible conduit structure includes a distal balloon-receiving section having at least a balloon-receiving lumen and two perfusion lumens and a proximal blood-uptake section having only a balloon-receiving lumen and a balloon catheter shaft-receiving lumen.

4. A perfusion shunt device as in claim 3, wherein the balloon catheter shaft-receiving lumen is axially split.

5. A perfusion shunt device as in claim 4, further having a balloon-receiving port disposed between the balloon-receiving section and the blood-uptake section.

6. A perfusion shunt device as in claim 1, further comprising a proximal shaft structure extending proximally from the flexible conduit structure.

7. A perfusion shunt device as in claim 6, wherein the proximal shaft structure has a more flexible distal portion and a less flexible proximal portion.

8. A perfusion shunt device as in claim 6, wherein the proximal shaft structure has a lumen which is connected to pass fluids to the perfusion path in the flexible conduit structure.

9. A perfusion shunt device as in claim 8, wherein the flexible conduit structure has a length in the range from 2.5 cm to 50 cm and a diameter below 2 mm suitable for insertion from a coronary ostium into the coronary vasculature, wherein the more flexible distal portion of the proximal shaft structure has a length in the range from 10 cm to 25 cm and a diameter below 1.5 mm suitable for insertion through the aortic arch, and wherein the less flexible proximal portion of the proximal shaft structure has a length in the range from 80 cm to 120 cm and a diameter below 1 mm suitable for insertion through the femoral artery to the aortic arch.

10. A perfusion shunt device as in claim 6, further comprising a tether extending from the proximal shaft structure through at least a proximal portion of the flexible conduit structure.

11. A perfusion shunt device as in claim 10, wherein the tether extends at least from the distal end of the less flexible proximal portion of the shaft structure to the proximal portion of the flexible conduit structure.

12. A perfusion shunt device as in claim 1, wherein the means for removably securing over the angioplasty balloon comprises a non-distensible flexible pouch which receives the balloon.

13. A perfusion shunt device as in claim 12, wherein the non-distensible pouch is sized smaller than the angioplasty balloon when fully expanded, wherein the total expanded size of the pouch and flexible conduit structure is substantially the same as that of the expanded balloon.

14. A perfusion shunt device as in claim 12, wherein the flexible conduit structure comprises a tubular body having a radially expansible lumen for removably securing the angioplasty balloon and at least one additional lumen or channel for defining the blood perfusion path, wherein the expansible lumen is substantially non-distensible beyond its fully expanded size.

15. A perfusion shunt device as in claim 14, wherein the said at least one additional lumen includes a plurality of perfusion ports along its length.

16. A perfusion shunt device as in claim 15, further comprising a proximal shaft structure having at least one lumen in fluid communication with said at least one additional lumen in the flexible conduit structure, whereby liquid agents can be introduced through the shaft into the conduit structure and released through the perfusion ports.

17. A perfusion shunt device as in claim 6, further comprising a radiopaque marker near the junction of the proximal end of the flexible conduit structure and a distal end of the proximal shaft structure.

18. A perfusion shunt device as in claim 1, further comprising a radiopaque marker aligned with the balloon-securing means.

19. A perfusion shunt device as in claim 18, comprising at least two axially spaced-apart radiopaque markers.

20. A perfusion shunt device as in claim 6, wherein at least a distal portion of the proximal shaft structure has an increased flexibility in the distal direction.

21. A perfusion shunt device as in claim 20, wherein the proximal shaft structure is tubular and the variable flexibility is provided by a pattern of axially spaced-apart grooves or by a spiral groove.

22. A perfusion shunt device for use in combination with an angioplasty balloon catheter, said device comprising:

a perfusion tube having a proximal end, a distal end, at least one blood perfusion lumen, and a plurality of axially spaced-apart perfusion ports which permit blood flow into and out of the perfusion lumen, wherein the length from the proximal end to the distal end is at least 2.5 cm; and a non-distensible pouch for receiving the angioplasty balloon secured to the perfusion tube, said pouch having an elongate balloon-receiving cavity which is disposed parallel to the blood perfusion lumen.

23. A perfusion shunt device as in claim 22, wherein the flexible conduit structure includes at least a balloon receiving lumen and two perfusion lumens along its entire length.

24. A perfusion shunt device as in claim 22, wherein the flexible conduit structure includes a distal balloon-receiving section having at least a balloon-receiving lumen and two perfusion lumens and a proximal blood-uptake section having only a blood-uptake lumen and a balloon catheter shaft-receiving lumen.

25. A perfusion shunt device as in claim 24, wherein the balloon catheter shaft-receiving lumen is characterized by either a single continuous split, a plurality of axially and circumferentially spaced-apart splits, or by a plurality of cut-outs.

26. A perfusion shunt device as in claim 25, further having a balloon-receiving port disposed between the balloon-receiving section and the blood-uptake section.

27. A perfusion shunt device as in claim 22, further comprising a proximal shaft structure extending proximally from the perfusion tube.

28. A perfusion shunt device as in claim 27, wherein the proximal shaft structure has a more flexible distal portion and a less flexible proximal portion.

29. A perfusion shunt device as in claim 27, wherein the proximal shaft structure has a lumen which is connected to pass fluids to the perfusion lumen in the flexible conduit structure.

30. A perfusion shunt device as in claim 28, wherein the perfusion tube has a length in the range from 2.5 cm to 50 cm and a diameter below 2 mm suitable for insertion from a coronary ostium into the coronary vasculature, wherein the more flexible distal portion of the proximal shaft structure has a length in the range from 10 cm to 25 cm and a diameter below 1.5 mm suitable for insertion through the aortic arch, and wherein the less flexible proximal portion of the proximal shaft structure has a length in the range from 80 cm to 120 cm and a diameter below 1 mm suitable for insertion through the femoral artery to the aortic arch.

31. A perfusion shunt device as in claim 27, further comprising a tether extending from the proximal shaft structure through at least a proximal portion of the perfusion tube.

32. A perfusion shunt device as in claim 31, wherein the tether extends at least from the distal end of the less flexible proximal portion of the shaft structure to the proximal portion of the perfusion tube.

33. A perfusion shunt device as in claim 22, wherein the non-distensible pouch is sized smaller than the angioplasty balloon when fully expanded, wherein the total expanded size of the pouch and flexible conduit structure is substantially the same as that of the expanded balloon.

34. A perfusion shunt device as in claim 22, wherein the proximal shaft structure is tubular with at least one lumen in fluid communication with said blood perfusion lumen, whereby liquid agents can be introduced through the shaft into the perfusion tube and released through the perfusion ports.

35. A perfusion shunt device as in claim 22, further comprising a radiopaque marker near the junction of the proximal end of the perfusion tube and the distal end of the proximal shaft structure.

36. A perfusion shunt device as in claim 22, further comprising a radiopaque marker aligned with the non-distensible pouch.

37. A perfusion shunt device for use in combination with a balloon angioplasty catheter, said device comprising a flexible conduit structure having a proximal end, a distal end, at least one blood perfusion lumen extending from the proximal end to the distal end, and a balloon receiving lumen parallel to the blood-receiving lumen, wherein the balloon-receiving cavity has a non-distensible peripheral dimension for constraining balloon expansion.

38. A perfusion shunt device as in claim 37, wherein the balloon-receiving lumen has a tapered tip at its distal end with a distal port having a diameter in the range from 0.25 mm to 0.5 mm for receiving a guidewire.

39. A perfusion shunt device as in claim 38, wherein the tapered tip is expansible so that the distal port can be enlarged to a diameter in the range from 1 mm to 1.7 mm for receiving the balloon angioplasty catheter.

40. A perfusion shunt device as in claim 37, where in the balloon-receiving lumen has a generally straight tip with a non-distensible distal port having a diameter in the range from 1 mm to 1.7 mm for receiving the balloon angioplasty catheter.

41. A perfusion shunt device as in claim 37, wherein the balloon-receiving lumen has a proximal port with a diameter in the range from 1 mm to 1.7 mm for receiving the balloon angioplasty catheter.

42. A perfusion shunt device as in claim 37, further comprising a proximal shaft structure extending proximally from the flexible conduit structure.

43. A perfusion shunt device as in claim 42, wherein the proximal shaft structure has a more flexible distal portion and a less flexible proximal portion.

44. A perfusion shunt device as in claim 42, wherein the proximal shaft structure has a lumen which is connected to pass fluids to the perfusion path in the flexible conduit structure.

45. A perfusion shunt device as in claim 43, wherein the flexible conduit structure has a length in the range from 2.5 cm to 50 cm and a diameter below 2 mm suitable for insertion from a coronary ostium into the coronary vasculature, wherein the more flexible distal portion of the proximal shaft structure has a length in the range from 10 cm to 25 cm and a diameter below 1.5 mm suitable for insertion through the aortic arch, and wherein the less flexible proximal portion of the proximal shaft structure has a length in the range from 80 cm to 120 cm and a diameter below 1 mm suitable for insertion through the femoral artery to the aortic arch.

46. A perfusion shunt device as in claim 42, further comprising a tether extending from the proximal shaft structure through at least a proximal portion of the flexible conduit structure.

47. A perfusion shunt device as in claim 46, wherein the tether extends at least from the distal end of the less flexible proximal portion of the shaft structure to the proximal portion of the flexible conduit structure.

48. A perfusion shunt device as in claim 37, wherein the balloon-receiving cavity comprises a non-distensible flexible pouch formed as an expanded portion of the balloon-receiving lumen.

49. A perfusion shunt device as in claim 48, wherein the non-distensible pouch is sized radially smaller than the fully expanded angioplasty balloon, wherein the total radially expanded size of the pouch and flexible conduit structure is the same as that of the fully expanded balloon.

50. A perfusion shunt device as in claim 49, wherein the balloon-receiving lumen has a length of at least 2.5 mm and wherein the flexible pouch portion of the balloon-receiving lumen has a length in the range from 1.5 mm to 50 mm.

51. A perfusion shunt device as in claim 42, wherein the proximal shaft structure is tubular with at least one lumen in fluid communication with said blood perfusion lumen in the flexible conduit structure, whereby liquid agents can be introduced through the shaft into the perfusion lumen and released through the perfusion ports.

52. A perfusion shunt device as in claim 40, further comprising a radiopaque marker near the junction of the proximal end of the flexible conduit structure and the distal end of the proximal shaft structure.

53. A perfusion shunt device as in claim 52, further comprising a radiopaque marker aligned with the balloon-receiving means.

54. A perfusion shunt device as in claim 53, comprising at least two axially spaced-apart radiopaque markers.

55. A perfusion shunt device as in claim 42, wherein at least a distal portion of the proximal shaft structure has an increased flexibility in the distal direction.

56. A perfusion shunt device as in claim 55, wherein the proximal shaft structure is tubular and the variable flexibility is provided by a pattern of axially spaced-apart grooves or by a spiral groove.

57. A method for perfusing blood past a treatment site within a blood vessel, said method comprising:

providing a flexible conduit structure having a blood perfusion path and a non-distensible pouch for receiving an angioplasty balloon;

inflating the angioplasty balloon within the pouch at the treatment site at a first pressure, wherein blood perfusion past the inflated balloon is provided by the blood perfusion path.

58. A method as in claim 57, wherein balloon expansion is constrained by the non-distensible pouch and wherein, the peripheral dimension of the flexible conduit when the pouch is expanded by the angioplasty balloon at the first pressure is substantially equal to the unconstrained circumference of the angioplasty balloon when inflated at said first pressure.

59. A method as in claim 58, further comprising inflating the angioplasty balloon within the pouch at a second pressure greater than the first pressure, wherein the peripheral dimension of the flexible conduit is marginally increased.

60. A method as in claim 59, wherein the first pressure is in the range from 2 atmospheres to 6 atmospheres, the second pressure is in the range from 6 atmospheres to 12 atmospheres, and the marginal increase is in the range from 10% to 25%.

61. A method as in claim 57, wherein the non-distensible pouch is the same size as the fully inflated angioplasty balloon.

62. A method as in claim 57, wherein the flexible conduit structure is aligned over the angioplasty balloon while said balloon is in place within the blood vessel.

63. A method as in claim 57, wherein the flexible conduit structure is positioned over the angioplasty balloon outside of the blood vessel and wherein the flexible conduit structure and the balloon are advanced together within the blood vessel lumen to the treatment site over a guidewire.

64. An improved sleeve catheter of the type having a lumen for receiving an angioplasty catheter having a radiopaque marker aligned with an angioplasty balloon, wherein the improvement comprises a radiopaque marker on the sleeve catheter disposed so that said sleeve marker will align with said angioplasty balloon marker when the angioplasty catheter is properly aligned within the sleeve lumen.

65. An improved sleeve catheter as in claim 64, wherein the radiopaque marker in the sleeve has a length in the range from 1.5 mm to 10 mm and a width in the range from 0.25 mm to 1 mm.

66. An improved sleeve catheter as in claim 65, wherein the radiopaque marker is coiled.

67. A method for positioning a sleeve catheter over an angioplasty balloon catheter, said method comprising aligning a radiopaque marker on the sleeve over a radiopaque marker on the balloon catheter.

68. A method as in claim 67, wherein the marker on the sleeve is longer, but less wide than the marker on the balloon and wherein said aligning step includes centering the sleeve marker over the balloon marker.

69. A method as in claim 53, wherein the sleeve includes a pair of axially spaced-apart markers, wherein said aligning step includes centering the markers on either side of the balloon marker.

* * * * *